United States Patent [19]
Waki et al.

[11] Patent Number: 6,025,444
[45] Date of Patent: Feb. 15, 2000

[54] CINNAMIC ACID DERIVATIVE

[75] Inventors: Michinori Waki; Kenji Miyamoto; Yoshihiro Motani, all of Tokyo, Japan

[73] Assignees: Seikagaku Kogyo Kabushiki Kaisha (Seikagaku Corporation), Tokyo; Fuji Photo Film Co., Ltd., Kanagawa, both of Japan

[21] Appl. No.: 08/863,933

[22] Filed: May 27, 1997

Related U.S. Application Data

[63] Continuation-in-part of application No. 08/560,484, Nov. 17, 1995, abandoned.

[30] Foreign Application Priority Data

Nov. 17, 1994 [JP] Japan ..................................... 6-307050
Sep. 20, 1995 [JP] Japan ..................................... 7-264686

[51] Int. Cl.[7] ...................................................... C08F 8/32
[52] U.S. Cl. .......................... 525/293; 525/379; 525/298; 525/302; 526/238.2; 526/312
[58] Field of Search .......................... 526/238.2; 522/89; 575/379, 293, 298, 302

[56] References Cited

U.S. PATENT DOCUMENTS 5,462,976 10/1995 Matsuda et al. ............................ 522/74

FOREIGN PATENT DOCUMENTS

| | | |
|---|---|---|
| 0284632 | 5/1988 | European Pat. Off. . |
| 0298135 | 11/1989 | European Pat. Off. . |
| 0554898 | 11/1993 | European Pat. Off. . |

OTHER PUBLICATIONS

Makromol. Chem., 191, 2985–2991, (1990), Dieter Klemm et al, "Photoreactive cellulose derivatives with comb–like structure".

Chemical Abstracts, vol./22, No. 15, Apr. 10, 1995, Abstract No. 188059, T.M. Ibrahim et al, "Synthesis of certain 4–nitrocinnamoylamino acids and dipeptide derivatives of biological interest".

Bull. Soc. Chim. Belg., (1976), 85 (9), 647–56, A. DePooter et al, "N–Acylamino acids and peptides. IV. The synthesis of N–cinnamyl–, N–p–coumaryl–and N–cafeyglycine and –gylcyl–L–phenylalanine".

J. Am. Chem. Soc., (1990), 112(7), 2498–506, R. Popovitz–Biro et al, "A new series of amphiphilic molecules forming stable z–type (polar) Langmuir–Blodgett films".

J. Chromatogr., (1982), 234(1), 141–55, Christiaan F. Van Sumere et al, "Separation of some metabolically important aromatic N–acylamino acids of the benzoyl and cinnamoyl series . . . ".

J. Chromatographie, vol. 20, No. 1, 1965 pp. 48–69, C.F. Van Sumere et al, "A new thin–layer method of phenolic substances and coumarins".

Journal of the American Chemical Society, vol. 88, No. 20, 1966, DC US, pp. 4711–4713, Y. Shalitin et al, "Cooperative–effects of functional groups in peptides. II. Elimination reaction in . . . ".

*Primary Examiner*—Fred Zitomer
*Attorney, Agent, or Firm*—Sughrue, Mion, Zinn Macpeak & Seas, PLLC

[57] ABSTRACT

The invention provides a cinnamic acid derivative having a novel spacer introduced into cinnamic acid which is photodimerizable, a cinnamic acid-polysaccharide derivative photocurable with high sensitivity and efficiency obtainable by introducing the above cinnamic acid derivative into a host polysaccharide such as a glycosaminoglycan, and a photocrosslinked cinnamic acid-polysaccharide derivative obtainable by exposing the same cinnamic acid-polysaccharide derivative to ultraviolet light irradiation.

5 Claims, 9 Drawing Sheets

CINNAMIC ACID DERIVATIVE

CROSS-REFERENCE TO RELATED APPLICATION

This is a continuation-in-part application of U.S. application Ser. No. 08/560,484, filed Nov. 17, 1995 now abandoned.

FIELD OF THE INVENTION

This invention relates to a photodimerizable cinnamic acid derivative, a photocrosslinkable cinnamic acid-polysaccharide derivative, and a crosslinked cinnamic acid-polysaccharide derivative. The above cinnamic acid derivative and the cinnamic acid-polysaccharide derivative, which is produced by introduction of said cinnamic acid derivative into a host polysaccharide, are highly photoreactive compounds. Thus, on exposure to ultraviolet radiation, the cinnamic acid derivative undergoes an intermolecular crosslinking reaction (photodimerization reaction) to form a cyclobutane ring, thus enabling production of an insoluble crosslinked cinnamic acid-polysaccharide derivative from said cinnamic acid-polysaccharide derivative. When a glycosaminoglycan, biogenic substance, is selected as the host polysaccharide, the resulting photocrosslinked cinnamic acid-polysaccharide derivative can be a useful medical material having biocompatibility, bioresorptivity and other desirable characteristics.

BACKGROUND OF THE INVENTION

Although a large number of photodimerizable compounds are known today, little information is available on the introduction of photocrosslinking groups into water-soluble host polysaccharides. Technology is known in which photocrosslinked compounds were prepared by introducing various stilbazonium derivatives into the water-soluble polymer polyvinyl alcohol (JP-B-Sho-56-5762, JP-B-Sho-56-54155 and JP-B-Sho-61-12888, the term "JP-BE" used herein means examined published Japanese patent application), but the objective of this technology is the immobilization of enzymes and bacteria and, moreover, the host polymers for introduction of photocrosslinking groups are chemically synthesized polymers. In these cases, in order to improve photoreactivity, the photodimerizable compounds are structurally modified to provide variations in absorption of ultraviolet region and its sensitivity.

EP-A-0 554 898 or JP-A-Hei-6-73102 describes a technology in which cinnamic acid is introduced into the natural polymer glycosaminoglycan and the resulting derivative is crosslinked by means of ultraviolet irradiation (the term "JP-A" used herein means unexamined published Japanese patent application). Almost all of the examples given are directed to the preparation of a photocrosslinkable glycosaminoglycan compound through the direct introduction of cinnamic acid by way of ester linkage to the hydroxyl group of the host glycosaminoglycan, without the use of a spacer group, and the subsequent exposure of the compound to ultraviolet irradiation to provide a photocrosslinked product.

This technology has the disadvantage that cinnamic acid must be introduced at a very high degree of substitution [DS (%): degree of substitution=100×(the number of moles of cinnamic acid introduced per repeating constituent saccharide unit)] to a sufficient extent and moreover that the efficiency of the photoreaction is poor. For example, DS necessary for induction of photocrosslinking reaction of a hyaluronic acid derivative incorporated with such photoreactive group (photodimerizable-crosslinkable group) as cinnamoyl group is fairly high (10% or more). In many of said hyaluronic acid derivative, intrinsic properties such as biodegradability, biocompatibility, non-toxicity, non-antigenicity, high swelling, etc. have been lost.

To cause crosslinking reaction of a hyaluronic acid derivative with low DS, it is favorable to use a hyaluronic acid with higher molecular weight. In this case, however, DS of cinnamoyl group is high and thus severe reaction conditions are required in accordance with the method developed previously. It is known that a hyaluronic acid is easily degraded to low molecule by heating, stirring, change of pH, etc. and that this degradation tendency is increased as the molecular weight becomes higher. Namely, the conventional technique accompanies side reactions such as degradation of hyaluronic acid to low molecule. Moreover, the hyaluronic acid derivative with high DS (10% or more) tends to cause stimulation in a living body, possibly damaging the outstanding intrinsic properties of a hyaluronic acid.

The above-described patent application further presents an example in which cinnamic acid was introduced into the carboxyl group of a glycosaminoglycan using a diamine as the spacer but this method is not satisfactory in the selectivity of the cinnamic acid substitution reaction.

SUMMARY OF THE INVENTION

A first object of this invention is to provide a cinnamic acid derivative by introduction of a spacer into photodimerizable cinnamic acid.

A second object of the invention is to provide a cinnamic acid-polysaccharide derivative, which is photodimerizable with high sensitivity and high efficiency, through the introduction of said cinnamic acid derivative into a host polysaccharide such as a glycosaminoglycan and a crosslinked cinnamic acid-polysaccharide derivative produced by photocrosslinking said cinnamic acid-polysaccharide derivative.

As the result of intensive research, the inventors of this invention succeeded in accomplishing the above-mentioned objects by way of the following invention:

1) A cinnamic acid derivative having a photodimerizable-crosslinkable group represented by any of the formulas (1)–(3) or a salt thereof;

$$R^1\text{—}A\text{—}A\text{—}H \quad (1)$$

$$R^1\text{—}B\text{—}OH \quad (2)$$

$$R^2\text{—}C\text{—}C \quad (3)$$

wherein $R^1$ represents a group of the formula (4):

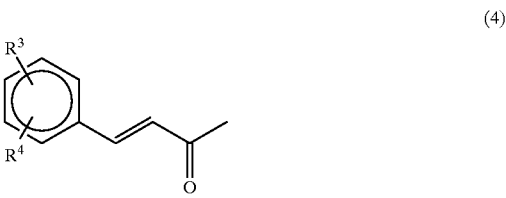

(4)

wherein $R^3$ $R^4$ independently represent a hydrogen atom, a nitro group, an amino group, a hydroxyl group or a $C_{1-4}$ alkoxy group;

$R^2$ represents a group of the formula (5):

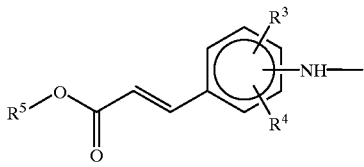
(5)

wherein $R^3$ $R^4$ are as defined above; $R^5$ represents a lower alkyl group;

A—H represents an intramolecularly amino—and hydroxy—containing compound residue represented by any of the formulas (6)—(9):

$$-(CH_2)_n-NH_2 \qquad (6)$$

wherein n represents a whole number of 3–18, $$-(CH_2CH_2)_m-NH_2 \qquad (7)$$

wherein m represents a whole number of 2–10, $$-O-CHR^6CH(COOR^7)-NH_2 \qquad (8)$$

wherein $R^6$ represents a hydrogen atom or a lower alkyl group;
$R^7$ represents a lower alkyl group, $$-O-(CH_2)_l-NHCO-CHR^8-NH_2 \qquad (9)$$

wherein l represents a whole number of 2–18; $R^8$ represents the side chain of an α-amino acid residue;

B—OH represents an amino acid residue of the formula (10):

$$-NH-(CH_2)_k-COOH \qquad (10)$$

wherein k represents a whole number of 1–18;

C—H represents an amino acid residue of the formula (11) or (12):

$$-CO-(CH_2)_k-NH_2 \qquad (11)$$

wherein k is as defined above, $$-(COCHR^8NH)_i-H \qquad (12)$$

wherein i represents a whole number of 1–6; $R^8$ is as defined above;

2) A cinnamic acid-polysaccharide derivative into which the cinnamic acid derivative of the above 1) is introduced represented by any of the formulas (13)–(15):

$$R^1-A-P^1 \qquad (13)$$

$$R^1-B-P^2 \qquad (14)$$

$$R^2-C-P^1 \qquad (15)$$

wherein $R^1$ represents a group of the formula (4):

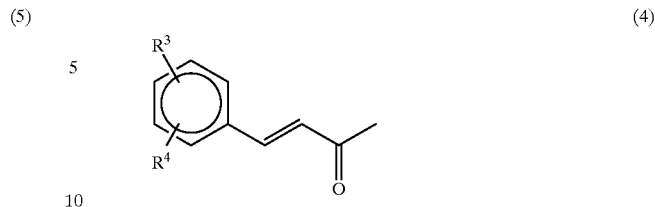
(4)

wherein $R^3$ and $R^4$ independently represent a hydrogen atom, a nitro group, an amino group, a hydroxyl group or a $C_{1-4}$ alkoxy group;
$R^2$ represents a group of the formula (5):

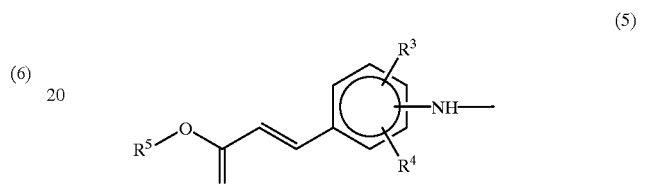
(5)

wherein $R^3$ and $R^4$ are as defined above; $R^5$ represents a lower alkyl group;

A— represents an amino- and hydroxy-containing compound residue represented by any of the formulas (6')–(9'):

$$-O-(CH_2)_n-NH \qquad (6')$$

wherein n represents a whole number of 3–18, $$-(O-CH_2CH_2)_m-NH \qquad (7')$$

wherein m represents a whole number of 2–10, $$-O-CHR^6CH(COOR^7)-NH \qquad (8')$$

wherein $R^6$ represents a hydrogen atom or a lower alkyl group; $R^7$ represents a lower alkyl group, $$-O-(CH_2)_l-NHCO-CHR^8-NH \qquad (9')$$

wherein l represents a whole number of 2–18; $R^8$ represents the side chain of an α-amino acid residue;

B— represents an amino acid residue of the formula (10'):

$$-NH-(CH_2)_k-CO \qquad (10')$$

wherein k represents a whole number of 1–18;
C— represents an amino acid residue of the formula (11') or (12'):

$$-CO-(CH_2)_k-NH \qquad (11')$$

wherein k is as defined above, $$-(COCHR^8NH)_i \qquad (12')$$

wherein i represents a whole number of 1–6; $R^8$ is as defined above;

$P^1$ represents a carboxy-containing polysaccharide residue; $P^2$ represents an amino- or hydroxy-containing polysaccharide residue;

the A—$P^1$ linkage is the amide bond formed between the terminal amino group of the formula (6'), (7'), (8') or (9') and the carboxyl group of $P^1$; the B—$P^2$ linkage is the amide bond formed between the terminal carboxyl group of the formula (10') and the amino group of P² or the ester bond formed between the terminal carboxyl group of the formula (10') and the hydroxyl group of P²; and the C—P¹ linkage is the amide bond formed between the terminal amino group of the formula (11') or (12') and the carboxyl group of P¹;

with the proviso that, when the cinnamic acid-polysaccharide derivative is represented by the formula (13), the photodimerizable-crosslinkable group is introduced into the cinnamic acid-polysaccharide derivative at a degree of substitution of 0.05–5.0% to a repeating constituent saccharide unit of the polysaccharide.

3) The cinnamic acid-polysaccharide derivative of the above 2) wherein the photodimerizable-crosslinkable group is introduced into the cinnamic acid-polysaccharide derivative represented by the formula (15) at a degree of substitution of 0.05–5.0% to a repeating constituent saccharide unit of the polysaccharide, and the polysaccharide is a hyaluronic acid;

4) The cinnamic acid-polysaccharide derivative of the above 2) wherein the polysaccharide is a glycosaminoglycan or a polyaminosaccharide;

5) The cinnamic acid-polysaccharide derivative of the above 4) wherein the glycosaminoglycan is a member selected from the group consisting of hyaluronic acid, chondroitin sulfate, dermatan sulfate, chondroitin, heparin, heparan sulfate and keratan sulfate;

6) The cinnamic acid-polysaccharide derivative of the above 4) wherein the glycosaminoglycan is a hyaluronic acid.

7) The cinnamic acid-polysaccharide derivative of the above 6) wherein the hyaluronic acid has a number average molecular weight of 100,000–5,000,000;

8) The cinnamic acid-polysaccharide derivative of the above 4) wherein the polyaminosaccharide is a chitin or chitosan;

9) A crosslinked cinnamic acid-polysaccharide derivative wherein the cinnamic acid-polysaccharide derivative of the above 2) is crosslinked by containing a cyclobutane ring produced by photodimerization of $R^1$ and $R^1$, $R^2$ and $R^2$, or $R^1$ and $R^2$ in the cinnamic acid-polysaccharide derivative represented by the formula (13), (14) or (15) or in a mixture thereof;

10) The crosslinked cinnamic acid-polysaccharide derivative of the above 9) wherein the cinnamic acid-polysaccharide derivative is crosslinked by containing a cyclobutane ring produced by photodimerization of $R^1$ and $R^1$ in the cinnamic acid-polysaccharide derivative represented by the formula (13);

11) The crosslinked cinnamic acid-polysaccharide derivative of the above 9) wherein the cinnamic acid-polysaccharide derivative is crosslinked by containing a cyclobutane ring produced by photodimerization of $R^1$ and $R^1$ in the cinnamic acid-polysaccharide derivative represented by the formula (14);

12) The crosslinked cinnamic acid-polysaccharide derivative of the above 9) wherein the cinnamic acid-polysaccharide derivative is crosslinked by containing a cyclobutane ring produced by photodimerization of $R^2$ and $R^2$ in the cinnamic acid-polysaccharide derivative represented by the formula (15);

13) The crosslinked cinnamic acid-polysaccharide derivative of the above 9) wherein the cinnamic acid-polysaccharide derivative contains the cyclobutane ring produced by photodimerization of $R^1$ and $R^1$, $R^2$ and $R^2$, or $R^1$ and $R^2$ and a geometrically isomerized $R^1$ or $R^2$ produced by photoisomerization, each by irradiating the cinnamic acid-polysaccharide derivative represented by the formula (13), (14) or (15) with ultraviolet light;

14) The crosslinked cinnamic acid-polysaccharide derivative of the above 9) wherein the photodimerizable-crosslinkable group is introduced into the cinnamic acid-polysaccharide derivative represented by the formulas (13) and/or (15) at a degree of substitution of 0.05–5.0% to a repeating constituent saccharide unit of the polysaccharide;

15) The crosslinked cinnamic acid-polysaccharide derivative of the above 9), which is a water-insoluble crosslinked hyaluronic acid derivative in the form of film, gel or powder;

16) The crosslinked cinnamic acid-polysaccharide derivative of the above 9) wherein the polysaccharide is a glycosaminoglycan or a polyaminosaccharide;

17) The crosslinked cinnamic acid-polysaccharide derivative of the above 16) wherein the glycosaminoglycan is a member selected from the group consisting of hyaluronic acid, chondroitin sulfate, dermatan sulfate, chondroitin, heparin, heparan sulfate and keratan sulfate;

18) The crosslinked cinnamic acid-polysaccharide derivative of the above 16) wherein the glycosaminoglycan is a hyaluronic acid;

19) The crosslinked cinnamic acid-polysaccharide derivative of the above 18) wherein the hyaluronic acid has a number average molecular weight of 100,000–5,000,000;

20) The crosslinked cinnamic acid-polysaccharide derivative of the above 16) wherein the polyaminosaccharide is a chitin or chitosan;

21) A process for producing a cinnamic acid-polysaccharide derivative represented by the formula (13) or (15):

(13)

(15)

wherein $R^1$ represents a group of the formula (4);

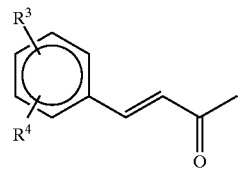

(4)

wherein $R^3$ and $R[]$ independently represent a hydrogen atom, a nitro group, an amino group, a hydroxyl group or a $C_{1-4}$ alkoxy group;

$R^2$ represents a group of the formula (5):

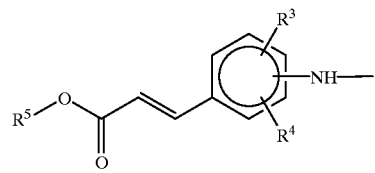

(5)

wherein $R^3$ and $R^4$ are as defined above; $R^5$ represents a lower alkyl group;

A— represents an amino- and hydroxy-containing compound residue represented by any of the formulas (6')–(9'):

$$—O—(CH_2)_n—NH \quad (6')$$

wherein n represents a whole number of 3–18, $$—(O—CH_2CH_2)_m—NH \quad (7')$$

wherein m represents a whole number of 2–10, $$—O—CHR^6CH(COOR^7)—NH \quad (8')$$

wherein $R^6$ represents a hydrogen atom or a lower alkyl group;
$R^7$ represents a lower alkyl group, $$—O—(CH_2)_l—NHCO—CHR^8—NH \quad (9')$$

wherein l represents a whole number of 2–18; $R^8$ represents the side chain of an α-amino acid residue;
C— represents an amino acid residue of the formula (11') or (12'):

$$—CO—(CH_2)_k—NH \quad (11')$$

wherein k is as defined above, $$—(COCHR^8NH)_i \quad (12')$$

wherein i represents a whole number of 1–6; $R^8$ is as defined above;
$P^1$ represents a carboxy-containing polysaccharide residue; the A—$P^1$ linkage is the amide bond formed between the terminal amino group of the formula (6'), (7'), (8') or (9') and the carboxyl group of $P^1$; and the C—$P^1$ linkage is the amide bond formed between the terminal amino group of the formula (11') or (12') and the carboxyl group of $P^1$;
which comprises the steps of
(A) dissolving a polysaccharide in water or in water containing a water-miscible organic solvent and
(B) reacting the carboxyl group of the polysaccharide with the amino group of a cinnamic acid derivative having a photodimerizable-crosslinkable group represented by the formula (1) or (3);

$$R^1—A—H \quad (1)$$

$$R^2—C—H \quad (3)$$

wherein $R^1$ represents a group of the formula (4):

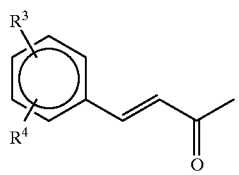
(4)

wherein $R^3$ and $R^4$ independently represent a hydrogen atom, a nitro group, an amino group, a hydroxyl group or a $C_{1-4}$ alkoxy group;

$R^2$ represents a group of the formula (5):

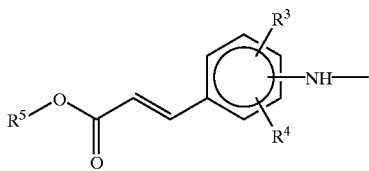
(5)

wherein $R^3$ and $R^4$ are as defined above; $R^5$ represents a lower alkyl group;
A—H represents an amino- and hydroxy-containing compound residue represented by any of the formulas (6)–(9):

$$—O—(CH_2)_n—NH_2 \quad (6)$$

wherein n represents a whole number of 3–18, $$—(O—CH_2CH_2)_m—NH_2 \quad (7)$$

wherein m represents a whole number of 2–10, $$—O—CHR^6CH(COOR^7)—NH_2 \quad (8)$$

wherein $R^6$ represents a hydrogen atom or a lower alkyl group;
$R^7$ represents a lower alkyl group, $$—O—(CH_2)_l—NHCO—CHR^8—NH_2 \quad (9)$$

wherein l represents a whole number of 2–18; RO represents the side chain of an α-amino acid residue;
C—H represents an amino acid residue of the formula (11) or (12):

$$—CO—(CH_2)_k—NH \quad (11)$$

wherein k is as defined above, $$—(COCHR^8NH)_i—H \quad (12)$$

wherein i represents a whole number of 1–6; $R^8$ is as defined above, in the presence of a water-soluble carbodiimide and an auxiliary condensing agent;

22) The process of the above 21) wherein the photodimerizable-crosslinkable group is introduced into the cinnamic acid-polysaccharide derivative represented by the formula (13) at a degree of substitution of 0.05–5.0% to a repeating constituent saccharide unit of the polysaccharide;

23) A process for producing a cinnamic acid-glycosaminoglycan derivative having a photodimerizable-crosslinkable group represented by the formula (14):

$$R^1—B—P^2 \quad (14)$$

wherein R$^1$ represents a group of the formula (4):

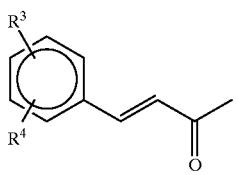
(4)

wherein R$^3$ and R$^4$ independently represent a hydrogen atom, a nitro group, an amino group, a hydroxyl group or a C$_{1-4}$ alkoxy group;

B— represents an amino acid residue of the formula (10'):

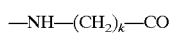
—NH—(CH$_2$)$_k$—CO (10')

wherein k represents a whole number of 1–18;

P$^2$ represents a glycosaminoglycan residue; and the B—P$^2$ linkage is the amide bond formed between the terminal carboxyl group of the formula (10') and the amino group of P$^2$;

which comprises the steps of (A) activating the carboxyl group of a cinnamic acid derivative represented by the formula (2):

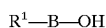
R$^1$—B—OH (2)

wherein R$^1$ represents a group of the formula (4):

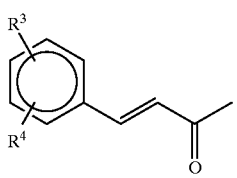
(4)

wherein R$^3$ and R$^4$ independently represent a hydrogen atom, a nitro group, an amino group, a hydroxyl group or a C1-alkoxy group; and B—OH represents an amino acid residue of the formula (10):

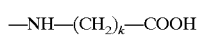
—NH—(CH$_2$)$_k$—COOH (10)

wherein k represents a whole number of 1–18; and (B) adding the activated cinnamic acid derivative to an organic solvent of an amine or ammonium salt of a glycosaminoglycan in the presence of a basic catalyst;

24) A process for producing a cinnamic acid-polyaminosaccharide derivative having a photodimerizable-crosslinkable group represented by the formula (14):

R$^1$—B—P$^2$ (14)

wherein R$^1$ represents a group of the formula (4):

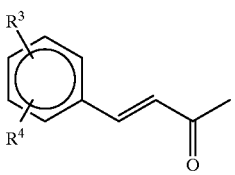
(4)

wherein R$^3$ and R$^4$ independently represent a hydrogen atom, a nitro group, an amino group, a hydroxyl group or a C$_{1-4}$ alkoxy group;

B— represents an amino acid residue of the formula (lau):

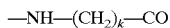
—NH—(CH$_2$)$_k$—CO (10')

wherein k represents a whole number of 1–18;

P$^2$ represents a polyaminosaccharide residue; and the B—P$^2$ linkage is the eater bond formed between the terminal carboxyl group of the formula (10') and the hydroxyl group of P$^2$;

which comprises the steps of (A) activating the carboxyl group of a cinnamic acid derivative represented by the formula (2):

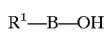
R$^1$—B—OH (2)

wherein R$^1$ represents a group of the formula (4);

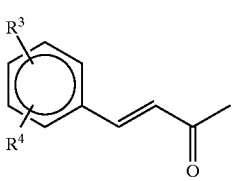
(4)

wherein R$^3$ and R$^4$ independently represent a hydrogen atom, a nitro group, an amino group, a hydroxyl group or a C$_{14}$ alkoxy group; and B—OH represents an amino acid residue of the formula (10):

—NH—(CH$_2$)$_k$—COOH (10)

wherein k represents a whole number of 1–18; and (B) adding the activated cinnamic acid derivative to an organic solvent of a polyaminosaccharide or a salt thereof;

25) The process of any one of the above 23) and 24) wherein the carboxyl group of the formula (2) is activated in the form of a cinnamic acid halide, a cinnamic anhydride or a mixed acid anhydride.

26) A process for producing a crosslinked cinnamic acid-polysaccharide derivative which comprises the steps of (A) dissolving a photodimerizable polysaccharide derivative obtained by the process of any one of the above 22)–24) in water or a water-miscible organic solvent, (B) removing the water or water-miscible organic solvent from the resulting solution, (C) forming the photodimerizable polysaccharide derivative into a shaped article and (D) irradiating the shaped article with ultraviolet light.

DETAILED DESCRIPTION OF THE INVENTION

Figure 1:
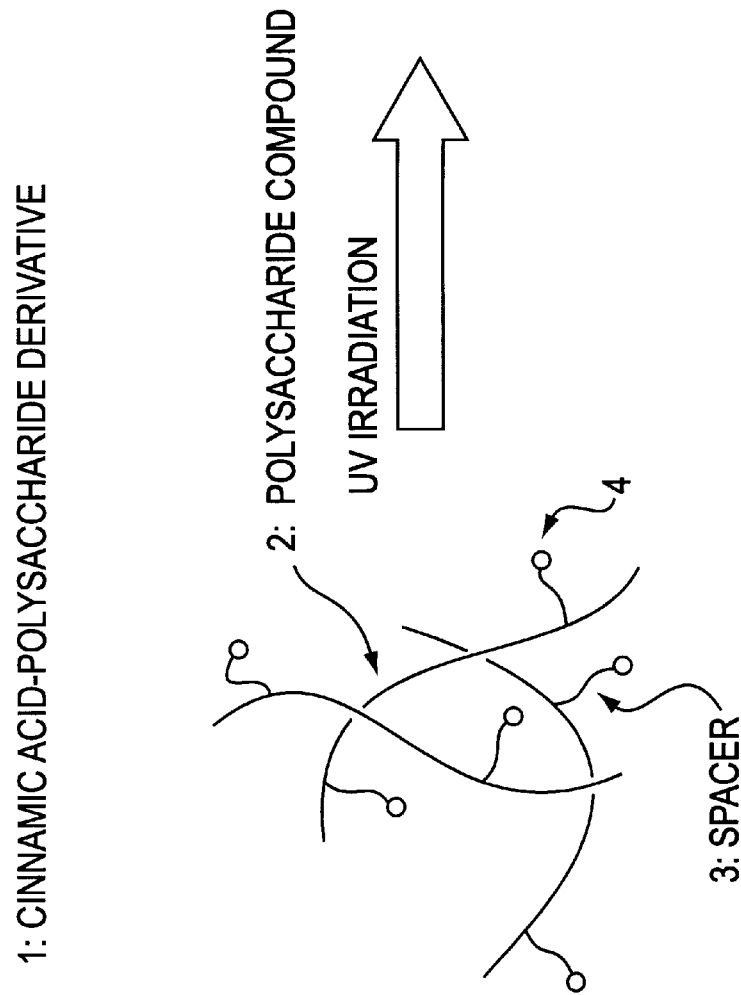
FIG. 1 shows concept illustrating the mutual photo-crosslinking reaction of a cinnamic acid derivative.

In the present invention, the DS (degree of substitution) is defined as a molar ratio (%) of the photodimerizable-crosslinkable group (cinnamic acid residue) introduced to the repeating constituent saccharide unit of the polysaccharide. When the polysaccharide is a glycosaminoglycan, the repeating constituent saccharide unit is a disaccharide. When the polysaccharide is a polyaminosaccharide, the repeating constituent saccharide unit is a monosaccharide.

When a polysaccharide compound corresponding to above-described $P^1$ or $P^2$ is a hyaluronic acid, this invention provides a photocrosslinkable hyaluronic acid derivative introduced with a cinnamic acid derivative corresponding to above-described formulas (1)–(3) as a photodimerizable-crosslinkable compound at mean 0.0005–0.05 per constituent disaccharide unit of hyaluronic acid as a preferred embodiment. Here, DS of the photocrosslinkable hyaluronic acid derivative having photodimerizable-crosslinkable group introduced at mean 0.0005–0.05 per constituent disaccharide unit of hyaluronic acid is 0.05–5.0%. When the polysaccharide is chondroitin sulfate in the cinnamic acid-polysaccharide derivative represented by the formula (15), the DS is preferably 0.05 to 10%.

In this invention, the inventors found the reaction conditions without degradation of high molecular weight hyaluronic acid (100,000–5,000,000) to low molecule and enabling the introduction of a photodimerizable-crosslinkable group. Namely, it was found that even the hyaluronic acid derivative introduced with photodimerizable-crosslinkable group at 1–100 per mean 4,000 monosaccharide per one molecule of hyaluronic acid can be crosslinked and insolubilized by irradiation of ultraviolet light for several minutes.

This invention provides technology that can afford a water-insoluble crosslinked hyaluronic acid derivative setting DS as very low as mentioned above by short time irradiation of light compared with conventional technology. In case of relatively low molecular weight polysaccharide such as chondroitin sulfate (KW 2,000–100,000) to insolubilize by photocrosslinking reaction, it is necessary to introduce a cinnamic acid derivative corresponding to above-described formulas (1)–(3) at level of about 1–20% of DS.

It is known that photodimerizable cinnamic acid and aminocinnamic acid compounds absorb ultraviolet (UV) light in a defined band around 280 rim to dimerize into truxillic acid or truxinic acid or derivatives thereof. This photodimerization reaction proceeds only under a certain quantity of ultraviolet radiation of the defined wavelength and does not proceed under ordinary light such as solar radiation. In this meaning, a photocrosslinked article obtainable by exposing a cinnamoylated glycosaminoglycan derivative, namely a compound available upon introduction of cinnamic acid into the functional group of a glycosaminoglycan, to ultraviolet irradiation is advantageous in that it can be provided by a clean photoreaction with high sensitivity and that the starting material, cinnamoylated glycosaminoglycan derivative, is easy to handle because it is hardly affected by sunlight and white light during storage.

However, in order to obtain a photocrosslinked article using the cinnamoylated glycosaminoglycan derivative previously developed as described in EP-A-0 554 898 or JP-A-Hei-6-73102, for example a hyaluronic acid with a number average molecular weight of 800,000, as the host polysaccharide, it is necessary to introduce 0.1–4 units (DS 10–400%) of cinnamic acid per disaccharide unit and irradiate the resulting compound with ultraviolet light for at least 30 minutes.

The inventors of this invention discovered that introduction of a flexible spacer between a host polysaccharide (e.g. a glycosaminoglycan, a polyaminosaccharide) and cinnamic acid results in a marked enhancement of photocurability so that the photocrosslinking reaction proceeds satisfactorily even at a more reduced degree of substitution with photocrosslinking groups.

The photocrosslinkable glycosaminoglycan derivative, which is a cinnamic acid-polysaccharide derivative containing a cinnamic acid derivative having such a spacer structure, can undergo photocrosslinking reaction at a reduced degree of substitution, taking a hyaluronic acid with a number average molecular weight of 100,000–5,000,000 as an example of said host polysaccharide, about 0.0005–0.05 units per disaccharide unit (DS 0.05–5%) and even with a UV exposure time of as short as-about 1–8 minutes.

The conventional cinnamic acid-polysaccharide derivative also undergoes photocrosslinking reaction upon exposure to ultraviolet radiation to form a giant molecule having a three-dimensional network structure via crosslinking groups and this crosslinked cinnamic acid-polysaccharide derivative is water-insoluble. However, the cinnamic acid-polysaccharide derivative (monomer) with molecular weight of the host polysaccharide in the range of 20,000–30,000 only produces a coarse network structure upon crosslinking and fails to produce a giant molecule. In order to enhance the density of crosslinking and achieve the necessary insolubilization, it is essential to employ a cinnamic acid-polysaccharide derivative with a fairly high degree of substitution (hereinafter "DS" is used to mean "degree of substitution").

In accordance with this invention wherein a spacer is introduced into the crosslinking group, a significant improvement is obtained in photocrosslinkability so that even when the monomer with a molecular weight of 20,000–30,000 is employed, a sufficient insolubilization can be achieved at a DS level of as low as 10% or less. Even a cinnamic acid-polysaccharide derivative with such a low DS value undergoes crosslinking to a sufficient extent in a short UV exposure time such as 1 to 10 minutes because of its high photoreactivity and the resulting crosslinked cinnamic acid-polysaccharide derivative is not only water-insoluble but also has a high water absorbing capacity and high strength properties.

The cinnamic acid derivatives of formulas (1)–(3) are now described in detail.

In formulas (1)–(3) [$R^1$—A—H (1), $R^2$—B—OH (2) and $R^2$, A—H, B—OH and C—H are the residues having the above-mentioned spacer function.

In formula (1), $R^1$ represented by formula (4) denotes a cinnamic acid residue having a vinylene group capable of photodimerizing to form a cyclobutane ring and $R^3$ and $R^4$ independently represent hydrogen, nitro, amino, hydroxyl or $C_{1-4}$ alkoxy, and hydrogen being preferred. The alkoxy that can be used includes methoxy, ethoxy, propoxy, isopropoxy, butoxy, isobutoxy and t-butoxy, etc. The positions of bonding of $R^3$ and $R^4$ to the benzene ring are not critical, unless any interaction of the substituent groups, steric hindrance and reduction of reactivity of the amino group occur.

A—H represents the residue of a compound having both an amino group and a hydroxyl group within the molecule as represented by any of formulas (6)–(9), which discharges the spacer function.

Thus, the formula $R^1$—A—H represents a cinnamic acid derivative in which the carbonyl group of cinnamic acid residue represented by $R^1$ is bonded to A—H and a spacer having an amino group is introduced into its terminus.

—O—(CH$_2$)$_n$—NH$_2$   (6)

wherein n represents a whole number of 3–18, preferably 4–8, more preferably 5 or 6. If n is 2 or less, the cinnamic acid-polysaccharide derivative (formula (13)) obtained by introduction of a compound of formula (1) into a host polysaccharide shows only a low efficiency of photo-crosslinking reaction. If n is 19 or greater, the efficiency of the reaction introducing a compound of formula (1) into the polysaccharide is lowered.

The residue of the above formula (6) is derived from an aminoalcohol such as aminoethanol, aminopropanol, aminobutanol, aminopentanol, aminohexanol, aminooctanoll aminododecanol, etc.

When A—H is the residue of the formula (6) derived from an aminoalcohol, the cinnamic acid derivative $R^1$—A—H can also be represented by the formula (1'-1)

H—NH(CR$'^1$R$'^2$)$_n$OCOCH=CH—Ph   (1'-1)

wherein R$'^1$ and R$'^2$ each represent a hydrogen atom, Ph represents a phenyl group which may have one or more substituents such as an alkyl or alkoxy group having 1 to 4 carbon atoms, an amino group, a hydroxyl group or a nitro group. n has the same definition as in the formula (6).

Typical examples of these compounds include cinnamic acid 3-aminopropyl ester, cinnamic acid 4-aminobutyl ester, cinnamic acid 5-aminopentyl ester, cinnamic acid 6-aminohexyl ester, cinnamic acid 8-aminooctyl ester, cinnamic acid 12-aminododecyl ester, etc.

In the formula (1'-1), R$'^1$ and R$'^2$ may be independently a hydrogen atom or a lower alkyl group, preferably having 1 to 4 carbon atoms.

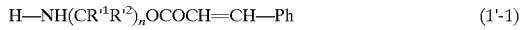

—(O—CH$_2$CH$_2$)$_m$—NH$_2$   (7)

wherein m represents a whole number of 2–10, preferably 2–5, more preferably 2 or 3. If m is 1 or less, the cinnamic acid-polysaccharide derivative will show only a low efficiency of photocrosslinking reaction, while an m value of 11 or more, the efficiency of the reaction introducing a compound of formula (1) into a host polysaccharide is lowered.

The residue of the above formula (7) is derived from a polyethylene glycolamine such as diethylene glycolamine, etc.

—O—CHR$^6$CH(COOR$^7$)—NH$_2$   (8)

wherein $R^6$ represents hydrogen or lower alkyl, preferably H or methyl; $R^7$ represents lower alkyl.

The residue of the above formula ( ia derived from a lower alkyl ester of a hydroxyamino acid such as serine or threonine, for instance.

When A—H is the residue of the formula (B) derived from a hydroxyamino acid, typical examples of the cinnamic acid derivative $R^1$—A—H include O-cinnamoyl serine methyl ester, O-cinnamoyl threonine methyl ester, etc.

—O—(CH$_2$)$_l$—NHCO—CHR$^8$—NH$_2$   (9)

wherein l represents a whole number of 2–18, preferably 2–8, more preferably 2 or 3; Re represents a side chain of an α-amino acid residue and is preferably hydrogen, methyl or isobutyl.

In the above formula (9), the moiety —CO—CHR$^8$—NH$_2$ is specifically derived from glycine, alanine, leucine or the like and the moiety —O—(CH$_2$)$_l$—NH— is specifically derived from aminoethanol, aminopropanol or the like.

The cinnamic acid derivative of formula (2) is then described.

$R^1$ has the same meaning as defined hereinbefore; B—OH represents an amino acid residue of the formula (10) and has the spacer function described hereinbefore.

—NH—(CH$_2$)$_k$—COOH   (10)

wherein k represents a whole number of 1–18, preferably 1–11, more preferably 3–5. The residue of the above formula (10) is derived from an amino acid such as β-alanine (aminopropionic acid), aminobutyric acid (aminobutanoic acid), aminocaproic acid (aminohexanoic acid), aminolauric acid (aminododecanoic acid), etc.

In formula (3), $R^2$ represents an aminocinnamic acid ester residue containing a vinylene group capable of photodimerizing to form a cyclobutane ring and optionally having a substituent or substituents represented by $R^3$ and $R^4$ which are as defined hereinbefore and each is preferably hydrogen; $R^5$ represents a lower alkyl group and is preferably methyl. The positions of bonding of $R^3$ and $R^4$ to the benzene ring are not critical unless any interaction of the substituent groups, steric hindrance and reduction of reactivity of the amino group occur.

The lower alkyl group used herein means an alkyl group having 1 to 4 carbon atoms.

C—H represents an amino acid residue of formula (11) or (12), which discharges the spacer function.

—CO—(CH$_2$)$_k$—NH$_2$   (11)

wherein k has the same meaning as defined hereinbefore.

The residue of the above formula (11) can be derived from any of amino acids essentially similar to those mentioned for the residue of formula (10).

When C—H is the residue of the formula (11) derived from an amino acid, the cinnamic acid derivative $R^2$—C—H can also be represented by the formula (2'-1-1).

H—A'—NH—Ph—CH=CHCOOR$'^3$   (2'-1-1)

wherein R'³ is an alkyl group, preferably having 1 to 4 carbon atoms, A' represents —NH(CR'⁴R'⁵)$_{h'}$CO—, wherein R'⁴ and R'⁵ represent a hydrogen atom, —Ph— represents a para-phenylene group which may have one or more substituents such as a lower alkyl or alkoxy group having 1 to 4 carbon atoms, an amino group, a hydroxyl group or a nitro group and h' is a whole number of 1 to 18, preferably 1 to 12.

Typical examples of these compounds include 4-(4-aminobutanamido)cinnamic acid methyl ester, 4-(6-aminohexamido)cinnamic acid methyl ester, 4-(12-aminododecanamido)cinnamic acid methyl ester, etc.

In the formula (2'-1-1), R'⁴ and R'⁵ may independently represent a hydrogen atom or a lower alkyl group, preferably having 1 to 4 carbon atoms.

—(COCHR⁸NH)$_i$—H     (12)

wherein i represents a whole number of 2–6, preferably 2–4, more preferably 2 or 3; R⁸ has the same meaning as defined hereinbefore and is preferably hydrogen.

The residue of the above formula (12) can be specifically derived from ordinary α-amino acids or oligomers thereof (e.g. glycine, glycylglycine, triglycine, etc.).

When C—H is the residue of the formula (12) derived from an amino acid, the cinnamic acid derivative R²—C—H can also be represented by the formula (2'-1-2).

H—A"—NH—Ph—CH=CHCOOR'³     (2'-1-2)

wherein A" represents —(NHCR'⁴R'⁵CO)$_{m'}$—; R'³, R'⁴, R'⁵ and —Ph— has the same definition as in the formula (2'-1-1); and m' is a whole number of 1 to 6, preferably 1 to 3.

Typical examples of these compounds include glycylaminocinnamic acid methyl ester, glycylglycylaminocinnamic acid methyl ester, triglycylaminocinnamic acid methyl ester, etc.

In the formula (2'-1-2), R'⁴ and R'⁵ may independently represent a hydrogen atom or a lower alkyl group, preferably having 1 to 4 carbon atoms.

[1] Synthesis of cinnamic acid derivatives

Processes for producing the cinnamic acid derivatives of formulas (1)–(3) are then described.

[1-1] The cinnamic acid derivative of formula (1) can be prepared, for example by the following reaction process.

In the following description, the moiety represented by —A—H in formula (1) is sometimes designated as —O—A¹—NH₂ for easier explanation of the reaction involved.

The objective compound of formula (1) can be obtained by subjecting the carboxyl group of a cinnamic acid derivative of the formula R¹—OH to react selectively with the hydroxyl group of a compound having both an amino group and a hydroxyl group (H₂N—A¹—OH). Generally, in order to react only said hydroxyl group efficiently and selectively, it is preferable to use the latter compound which has the amino group suitably protected beforehand (RaNH—A¹—OH). Then, the unprotected hydroxyl group of the said compound is subjected to form an ester linkage to provide an N-protected compound (1) Ra—NH—A¹—O—R¹. Removal of the amino-protecting group under suitable conditions gives the objective compound. Thus, by these two steps of esterification and deprotection, the objective cinnamic acid ester having a free amino group or a salt thereof can be obtained with good efficiency.

The synthetic reaction scheme involved is described below.

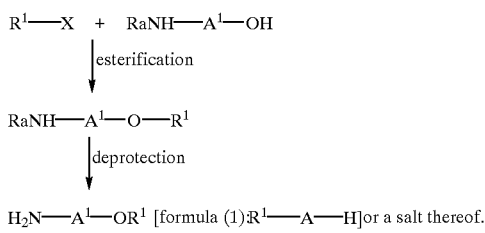

Each of these two steps is described in detail below.

First Step

The carboxyl group of a cinnamic acid derivative represented by the formula R¹-OH iv first activated [for example, in the form of a cinnamic acid halide of formula R¹—X (e.g. cinnamoyl chloride) cinnamic anhydride (R¹)₂O, or a mixed acid anhydride R'—O—R')] and this activated carboxyl group is subjected to react with the unprotected hydroxyl group of a compound (RaNH—A¹—OH) having both an amino group and a hydroxyl group (H₂N—A¹—OH) of which amino group has been protected beforehand to form an ester linkage, thus giving a compound (1) having a protected amino group, viz. RaNH—A¹—O—R¹. This reaction is preferably conducted in the presence of an acylation catalyst such as an N,N-dialkylaminopyridine (e.g. 4-dimethylaminopyridine, 4-pyrrolidinopyridine, etc.) or the like, and a neutralizer for the byproduct acid (e.g. a tertiary amine such as pyridine, triethylamine, etc. or an inorganic base such as sodium hydrogen carbonate).

The amino-protecting group that can be used in the above step is not particularly limited, provided that it can be removed under conditions not cleaving the cinnamic acid ester in the deprotection procedure in the second step.

Second Step

The amino-protecting group of the compound (RaNH—A¹—O—R¹) obtained in the above first step is removed under conditions not cleaving the cinnamic acid ester. The amino-protecting group that can be used includes t-butoxycarbonyl, benzyloxycarbonyl, and 9-fluorenylmethoxycarbonyl, etc. When a protective group such as t-butoxycarbonyl which can be removed by means of an acid is employed, the treatment with hydrogen chloride, hydrogen bromide, trifluoroacetic acid or the like simultaneously removes the amino-protecting group and produces the corresponding salt.

The hydrochloride of R¹—A—H, for example, can be synthesized in the following manner.

To the compound (Boc-NH—A¹—OH) employing t-butoxycarbonyl (Boc-) group as an N-protecting group which can be removed with an acid is added an organic solvent such as chloroform, etc. and then under ice-cooling an organic base such as triethylamine, etc., an acid halide of R¹—OH (R¹—X), and a basic catalyst (acylation catalyst) such as 4-dimethylamino-pyridine, etc. are added in the order mentioned. After stirring at room temperature, the mixture is diluted with an organic solvent such as ethyl acetate and washed, in the order, several times with each of a weakly acidic aqueous solution, water, a weakly alkaline aqueous solution, and with water, and a saturated aqueous sodium chloride solution in a separatory funnel. The organic layer is then dried over anhydrous sodium sulfate, etc. The resulting anhydrous sodium sulfate is then filtered off and the filtrate is concentrated under reduced pressure to provide the compound (RaNH—A¹—O—R¹) (First Step). To this compound (RaNH—A¹—O—R¹) is added an organic solvent solution of an acid, such as 1–5M HCl/dioxane, under ice-cooling and stirring to remove the amino-protecting group and, at the same time, to convert the product amine to the hydrochloride. An organic solvent for crystallization, such as ether, is then added and the resulting crystals are recovered by filtration. If required, this crystal crop is washed with an organic solvent and dried in vacuo to provide the compound ($R^1$—A—H hydrochloride) (Second Step).

[1-2] The cinnamic acid derivative of formula (2) can be produced by, for example, the following process.

In the following description, the moiety —B—OH in formula (2) is sometimes designated as —NH—$B^1$—COOH for ease of explanation of the reaction involved.

The carboxyl group of a cinnamic acid derivative of the formula $R^1$—OH is subjected to react selectively with the amino group of the amino acid ($H_2N$—$B^1$—COOH) having a free amino group and a free carboxyl group to form an amide linkage, whereby the objective compound of formula (2) can be obtained. Selective reaction with the amino group of said amino acid can be accomplished by two alternative methods, viz. (1) by dissolving the amino acid in an alkali solution and adding the compound available on activation of the carboxyl group of $R^1$—OH (Synthetic Process 1) or by providing an amino acid ester ($H_2N$—$B^1$—COORb) available on protection of the carboxyl group of the free amino acid, subjecting the carboxyl group of $R^1$—OH to react with the amino group of said amino acid ester, and removing the carboxyl-protecting group in the per se known manner (Synthetic Process 2). Each of these processes is described below.

---

Synthetic Process 1

$R^1$—X + $H_2N$—$B^1$—COOM (M: an alkali metal)
    ↓    amidation under alkaline conditions
    ↓    acid treatment
$R^1$—HN—$B^1$—COOH [formula (2): $R^1$—B—OH]

Synthetic Process 2

$R^1$—X + $H_2N$—$B^1$—COORb
    ↓    amidation
$R^1$—NH—$B^1$—COORb
    ↓    deprotection
$R^1$—B—OH

---

Each of the above synthetic processes is described in detail below.

[Synthetic Process 1]

The amino acid ($H_2N$—$B^1$—COOH) is dissolved in water and, under ice-cooling, the cinnamic acid derivative $R^1$—OH whose carboxyl group has been activated beforehand (for example, in the form of cinnamic acid halide $R^1$—X (e.g. cinnamoyl chloride), cinnamic acid anhydride $(R^1)_2O$, or mixed acid anhydride $R^1$—O—R') and an alkaline solution are slowly added dropwise so as to maintain the reaction solution under alkaline conditions. In this reaction, an organic solvent is preferably present concomitantly so that the highly hydrophobic cinnamic acid derivative will not be separated out. The preferred said organic solvent are dioxane, dimethylformamide, etc. and dioxane is most preferred. Preferable alkaline solution is an aqueous solution of sodium hydroxide or potassium hydroxide. As the reaction system is kept basic with an alkaline solution in the above manner, the carboxyl group of the amino acid forms a salt with the alkali metal and, at the same time, the amino group is deprotonated so that the reaction proceeds selectively with the amino group. The reaction mixture is then washed with an organic solvent in a separatory funnel, acidified, and extracted to isolate the objective compound $R^1$—B—OH.

[Synthetic Process 2]

The amino acid ester ($H_2N$—$B^1$—COORb) available on protection of the carboxyl group of an amino acid with a suitable protective group is dissolved or suspended in an anhydrous organic solvent and then under ice-cooling the compound available on activation of the carboxyl group of a cinnamic acid derivative $R^1$—OH (the same as defined above) and an organic base are added in that order. The carboxyl-protecting group mentioned above is not particularly limited provided that it does not affect properties of the product compound. Thus, for example, an ester of the carboxyl group such as methyl ester, ethyl ester, t-butyl ester, benzyl ester, etc. can be mentioned as the carboxyl-protecting groups. The unreacted compound can be removed by washing the reaction mixture with an acid or alkali in a separatory funnel. Depending on cases, the product is preferably purified by, for example, recrystallization.

The objective compound $R^1$—B—OH can be obtained by the cleavage of the carboxyl-protecting group from the above product compound ($R^1$—NH—$B^1$—COORb) under suitable conditions. For example, the methyl or ethyl ester can be cleaved by means of an alkali, the t-butyl ester with an acid, and the benzyl ester by hydrogenolysis.

The compound $R^1$—B—OH, for specific example, can be synthesized by the following processes.

[Synthetic Process 1]

The amino acid is dissolved in water and, under ice-cooling, a solution of an equimolar amount of a halide of $R^1$—OH (i.e. ($R^1$—X) in dioxane) and an aqueous solution of sodium hydroxide are slowly added dropwise so that the reaction solution will be maintained under alkaline conditions. After completion of dropwise addition, the reaction mixture is stirred at room temperature for 24 hours. The dioxane is then distilled away in vacuo and the aqueous layer is washed several times with ethyl acetate to remove the starting material. The aqueous layer is acidified with an acid, e.g., citric acid, and extracted several times with ethyl acetate. The organic layer extracted is dried over anhydrous sodium sulfate and concentrated under reduced pressure to provide the objective compound $R^1$—B—OH.

[Synthetic Process 2]

When a lower alkyl ester (i.e. $H_2N$—$B^1$—COORb), such as the methyl ester or ethyl ester, of said amino acid or a salt thereof is employed, the compound is first dissolved or suspended in chloroform. An organic base such as triethylamine is then added under ice-cooling so that the system may be maintained under neutral conditions and a solution of an equimolar amount of a halide (i.e. $R^1$—X) of $R^1$—OH to amino acid ester in chloroform is added. The mixture is stirred at room temperature for 24 hours. The reaction mixture is then diluted with ethyl acetate and successively washed several times with a weakly acidic aqueous solution, water, a weakly alkaline aqueous solution, and with water, and saturated aqueous sodium chloride solution, in a separatory funnel. The organic layer is dried over anhydrous sodium sulfate. The sodium sulfate is then filtered off and the filtrate is concentrated under reduced pressure to provide compound $R^1$—NH—$B_1$—COORb.

This compound is dissolved in methanol and, under ice-cooling, an excess of aqueous sodium hydroxide solution is added. This mixture is stirred at room temperature for 24 hours. The reaction mixture is then concentrated under reduced pressure and the residue is diluted with chloroform and water to extract the objective compound into the aqueous phase. This aqueous solution is acidified with an acid such as citric acid and extracted several times with ethyl acetate. The pooled organic layer is then washed with a saturated aqueous sodium chloride solution and the organic layer is dried over anhydrous sodium sulfate. The sodium sulfate is then filtered off and the filtrate is concentrated under reduced pressure to provide the objective compound $R^1$—B—OH.

[1-3] The cinnamic acid derivative of formula (3) can be produced by, for example, the following process.

In the following description, the moiety —C—H in formula (3) is sometimes designated as —CO—$C^1$—$NH_2$ for ease of explanation of the reaction involved.

The objective compound $R^2$—C—H can be obtained by subjecting the amino group of an ester of aminocinnamic acid of the formula $R^2$—H to react selectively with the carboxyl group of the amino acid ($H_2N$—$C^1$—COOH) to form an amide linkage. In order to achieve this selective reaction with the carboxyl group of the amino acid, it is generally preferable to use an amino acid whose amino group has been previously protected, i.e. an N-protected amino acid (RaNH—$C^1$—COOH). Thus, the amino group of $R^2$-H reacts with the carboxyl group of RaNH—$C^1$—COOH to form an amide linkage to give RaNH—$C^1$—CO—$R^2$; N-protected $R^2$—C—H (First Step). This compound is then deprotected under suitable conditions to provide the objective compound (Second Step). Thus, the objective compound can be prepared by the above two steps of amidation and deprotection. This synthetic reaction procedure is described as follows.

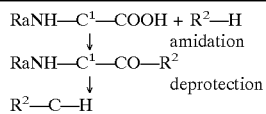

RaNH—$C^1$—COOH + $R^2$—H
↓ amidation
RaNH—$C^1$—CO—$R^2$
↓ deprotection
$R^2$—C—H Each of these steps is described in detail below.
[First Step]

The carboxyl group of the N-protected amino acid (RaNH—$C^1$—COOH) is first activated (for example, in the form of N-protected amino acid halide represented by RaNH—$C^1$—CO—X; N-protected amino acid anhydride represented by (RaNH—$C^1$—CO)$_2$O; or mixed acid anhydride represented by RaNH—$C^1$—CO—O—R') and then reacted with the amino group of the ester of aminocinnamic acid $R^2$—H in the presence of an organic base. The amino-protecting group of said N-protected amino acid is not particularly restricted, provided that the ester linkage of said ester of aminocinnamic acid is not cleaved under the conditions of deprotection of the protecting group. Preferred examples of the amino-protecting group are t-butoxycarbonyl, benzyloxycarbonyl, 9-fluorenylmethoxycarbonyl, etc. Particularly preferred is t-butoxycarbonyl. This reaction mixture is washed with an acid and an alkali to provide compound RaNH—$C^1$—CO—$R^2$ in a separatory funnel. Depending on the case, this product is preferably further purified by a routine purification procedure such as recrystallization and column chromatography.
[Second Step]

The amino-protecting group of the compound (RaNH—$C^1$—CO—$R^2$) obtained in the First Step is deprotected under suitable conditions to provide the objective compound $R^2$—C—H. Since the ester residue of the ester of aminocinnamic acid is a lower alkyl group, it is not appropriate to carry out deprotection by alkali saponification. Preferred is deprotection with an acid or by hydrogenolysis. More preferred is deprotection with an acid which forms a suitable salt at the same time. For example, in case of the use of t-butoxycarbonyl for the protective group, deprotection and salt formation using hydrogen chloride, hydrogen bromide, trifluoroacetic acid or the like acid can be utilized. In consideration of the introduction of the compound into a host polysaccharide in the next step, salt formation with an acid having a carboxyl group, such as trifluoroacetic acid, is not desirable. Thus, deprotection and salt formation using a hydrogen halide, particularly hydrogen chloride, is preferred.

A specific example of procedure for the synthesis of compound ($R^2$—C—H) is described below.

The compound (RaNH—$C^1$—COOH) is dissolved in an organic solvent such as chloroform, and then under ice-cooling an organic base such as triethylamine and a condensing agent such as dimethylphosphinothioyl chloride or pivaloyl chloride are added successively. The mixture is stirred at room temperature. To this solution, the compound $R^2$—H or a salt thereof and a base such as triethylamine are added under ice-cooling and the mixture is stirred at room temperature for tens of minutes to tens of hours. After completion of the reaction, the organic solvent is distilled off under reduced pressure and the residue is diluted with an organic solvent such as ethyl acetate and, using a separatory funnel, washed successively several times with a weakly acidic aqueous solution, water, a weakly alkaline aqueous solution, and with water, and saturated aqueous sodium chloride solution. The organic layer is then dried over anhydrous sodium sulfate or the like. The sodium sulfate is filtered off and the filtrate is concentrated under reduced pressure to give the compound (RaNH—$C^1$—CO—$R^2$). To this compound (RaNH—$C^1$—CO—$R^2$) is added a solution of an acid in an organic solvent, e.g. 1–5M HCl/dioxane, under-ice-cooling and the mixture is stirred. After completion of the reaction, an organic solvent such as ether is added and the resulting crystals are collected by filtration, washed with an organic solvent, and dried in vacuo to provide the hydrochloride of the compound ($R^2$—C—H).

[2] Synthesis of cinnamic acid-polysaccharide derivatives

The above spacer-incorporated cinnamic acid derivatives of formulas (1)–(3) are all new compounds. By reacting any of these derivatives with a polysaccharide compound (host polysaccharide) having a functional group capable of reacting with its functional group, a cinnamic acid-polysaccharide derivative of the corresponding formula (13)–(15) can be obtained.

$R^1$—A—$P^1$ (13)

$R^1$—B—$P^2$ (14)

$R^2$—C—$P^1$ (15)

wherein $R^1$, $R^2$, A, B and C are as defined hereinbefore; $P^1$ represents a carboxy-containing polysaccharide residue; $P^2$ represents an amino- or hydroxy-containing polysaccharide residue; the A—$P^1$ linkage is the amide bond formed between the terminal amino group of the residue of formula (6)–(9) and the carboxyl group of $P^1$; the B—$P^2$ linkage is the amide or ester bond formed between the terminal carboxyl group of the residue of formula (10) and either the amino group or the hydroxyl group of $P^2$; and the C—$P^1$ linkage is the amide bond formed between the terminal amino group-of the residue of formula (11) or (12) and the carboxyl group of pi.

The host polysaccharide compound containing $P^1$ or $P^2$ includes but is not limited to carboxyl-, amino-, and/or hydroxy-containing polysaccharides (e.g.

glycosaminoglycans, polyaminosaccharides, acidic polysaccharides, etc.), synthetic polymers (e.g. polyacrylic acid, polyimines, and polyhydroxy acids (e.g. polyglycolic acid, polylactic acid, etc.)), etc. Among them, polysaccharides are preferred and glycosaminoglycans are especially preferred. Among said glycosaminoglycans, hyaluronic acids, chondroitin sulfates (A, C, D, E and K), dermatan sulfate (chondroitin sulfate B), chondroitin, heparin, heparan sulfate, and keratan sulfate are exemplified. Particularly preferred are hyaluronic acid, chondroitin sulfate A, chondroitin sulfate C and heparin, all of which are readily available. Such polyaminosaccharides as chitin and chitosan are also preferred.

Purification following the reaction can be achieved by a routine procedure such as ethanol precipitation, dialysis or the like. After drying, DS can be determined by observing $^1$H-NMR (nuclear magnetic resonance) integral intensity or absorbance at 280 nm.

[2-1] The cinnamic acid-polysaccharide derivative of formula (13) or (15) can be produced by dissolving the polysaccharide containing the residue $P^1$ in either water or water containing a water-miscible organic solvent and reacting it with a cinnamic acid derivative of formula (1) or (3) in the presence of a water-soluble carbodiimide and an auxiliary condensing agent. The specific example of procedure for introduction of the cinnamic acid derivative is as follows. Said polysaccharide is dissolved in either water or water containing a water-miscible organic solvent and, the solution is gently stirred at a constant temperature of about 0° C.–40° C. (usually, 0° C.–35° C.), said water-soluble carbodiimide, said auxiliary condensing agent, and said cinnamic acid derivative are successively added.

The water-miscible organic solvent mentioned above includes dioxane, dimethylformamide (DMF), N-methylpyrrolidone, acetamide, alcohol (e.g. methanol, ethanol, etc.), pyridine, etc.

The proportion of the water-miscible organic solvent in said water containing a water-miscible organic solvent (organic solvent mixing ratio=$\Delta O$) can be expressed as follows.

$\Delta O$ (%)100×volume of water-miscible organic solvent/ volume of water containing the water-miscible organic solvent The value of $\Delta O$ is approximately 0–75%, preferably 30–50%.

The auxiliary condensing agent that can be used includes N-hydroxysuccinimide (HOSu), N-hydroxybenzotriazole (HOBt), etc. The auxiliary condensing agent not only functions to activate the carboxyl group of the polysaccharide but also functions to preclude the undesired O—N-acyl rearrangement.

The water-soluble carbodiimide (WSC) that can be used includes 1-ethyl-3-(3-dimethylaminopropyl)carbodiimide hydrochloride (EDC), 1-ethyl-3-(3-dimethylaminopropyl) carbodiimide methiodide, 1-cyclohexyl-3-(2-morpholinoethyl)carbodiimide hydrochloride, etc.

[2-2] The cinnamic acid-polysaccharide derivative of formula (14) can be synthesized by reacting a polysaccharide compound having the residue $P^2$ with a cinnamic acid derivative of formula (2). The reaction procedure depends on the mode of B—$P^2$ linkage, that is to say the functional group of $P^2$.

[2-2-1] In the case of the mode of linkage is an amide linkage, that is to say when the amino group of said polysaccharide compound is to be reacted with the carboxyl group of the cinnamic acid derivative of formula (2), said carboxyl group is first activated and the activated compound is reacted with said polysaccharide compound to form an amide linkage.

Concretely, the amino-containing polysaccharide compound is dissolved in acidic water or an acidic aqueous medium containing an alcohol or other organic solvent, and to the solution said cinnamic acid derivative of formula (2) having a pre-activated carboxyl group is added gradually at 0° C. room temperature. The method of activation of the carboxyl group is not particularly limited provided that the method can form an amide linkage with said amino group. The acid halide method, acid anhydride method, active ester method, etc., can be mentioned. For example, the objective cinnamic acid-polysaccharide derivative can be obtained by a reaction process which comprises the addition of a condensing agent (e.g. dimethylphosphinothioyl chloride) and a base (e.g. triethylamine) to a solution of said cinnamic acid derivative in an organic solvent (e.g. DMF) under ice-cooling to activate the carboxyl group of the derivative in the manner of mixed acid anhydride and the subsequent addition of the resulting mixed acid anhydride to a solution of said polysaccharide compound in an acidic aqueous alcohol medium (e.g. methanol-acetic acid) gradually at 0° C.—room temperature.

[2-2-2] In the case of the mode of linkage is an ester linkage, that is to say when the hydroxyl group of said polysaccharide compound is to be reacted with the carboxyl group of said cinnamic acid derivative of formula (2), said carboxyl group is first activated and the activated compound is reacted with hydroxyl group of said polysaccharide compound to form an ester linkage. This reaction can be carried out more efficiently in the presence of a catalyst in the reaction system.

Concretely, the hydroxy-containing polysaccharide compound is dissolved in an organic solvent and the cinnamic acid derivative of formula (2) whose carboxyl group has been activated beforehand is added gradually in the presence of said catalyst at 0° C.—room temperature.

Activation of the carboxyl group of the cinnamic acid derivative can be achieved in the same manner as described hereinbefore [2-2-1]. The organic solvent mentioned above may be any organic solvent that dose not inhibit the esterification reaction and is capable of dissolving said polysaccharide compound. As such organic solvent, DMF, N-methylpyrrolidone, dioxane, dimethyl sulfoxide (DMSO), etc. are included. The catalyst is not limited, provided that the esterification reaction is thereby promoted. 4-Dimethylaminopyridine is the preferred catalyst among the catalysts.

[3] Preparation of crosslinked cinnamic acid-polysaccharide derivatives

[3-1] The cinnamic acid-polysaccharide derivative of this invention can be prepared in a variety of forms for submission to photocrosslinking reaction. For example, such forms are solutions, films, gels, finely divided particles, and so on. When the host polysaccharide compound to be used is a highly hydrophilic and good biocompatible substance such as glycosaminoglycans, the cured articles prepared by subjecting said cinnamic acid-polysaccharide derivative to a photocrosslinking reaction are suitable for a variety of medical uses (biological tissue adhesion prevention material, vascular prosthesis material, coating agent, base material for control-release pharmaceutical preparations, contact lens material, bandage material, etc.) and the photocrosslinking by ultraviolet irradiation can be performed after the cinnamic acid-polysaccharide derivative has been processed into such end-use forms as described above depending on the application object.

For the processing of the cinnamic acid-polysaccharide derivative of this invention into such various forms, any of known technologies can be employed. Such processing can be made by judicious selection and appropriate adjustment of the amount of water or the proportion of a water-miscible organic solvent (organic solvent mixing ratio) in a solution of the cinnamic acid-polysaccharide derivative or a bulk solid of the cinnamic acid-polysaccharide derivative, temperature and pressure according to the intended purpose.

In the preparation of such a crosslinked cinnamic acid-polysaccharide derivative suited for medical application, the objective photocrosslinked cinnamic acid-polysaccharide article can be assured to be a sterile and substantially endotoxin-free status by taking care of the selection and handling to ensure a sterile state of the reagents, water and vessels for synthesis of starting materials and the water, vessels, and equipment for use in the molding and photocrosslinking of the cinnamic acid-polysaccharide derivative.

Concretely, the reaction mixture in which the cinnamic acid-polysaccharide derivative has been formed may be utilized as it is. As an alternative, the derivative formed is separated from the reaction mixture, purified and redissolved in, for example, water to provide an aqueous solution. A film can be manufactured by casting a solution (e.g. aqueous solution) of the cinnamic acid-polysaccharide derivative and removing the solvent from said solution. Gels can be manufactured by, for example, immersing the above film in water. Finely divided particles can be obtained by physical grinding of said film or gel.

[3-2] The crosslinked cinnamic acid-polysaccharide derivative of this invention is such that the photodimerizable crosslinking groups of cinnamic acid-polysaccharide derivative molecules form crosslinked cyclobutane rings and can be obtained by subjecting said cinnamic acid-polysaccharide derivative to ultraviolet irradiation.

The type of ultraviolet light is not particularly limited. The light source having wavelength of 200–600 nm, preferably 200–450 nm, is used. The light can be passed through a ultraviolet filter (e.g., Pyrexglass (trade name) filter, etc.) to cut the light having wavelength which is not necessary for photocrosslinking.

The means for ultraviolet irradiation include technology using a high-pressure mercury vapor lamp or a metal halide lamp as the light source and generally said film, gel or finely divided particles of cinnamic acid-polysaccharide derivative is exposed to UV light at 250–450 nm for 1 to 10 minutes. Compared with the photocrosslinking of the conventional photocrosslinkable, hyaluronic acid derivative having a high DS value which requires an irradiation time of 30 minutes, the technology of this invention features a marked reduction in the irradiation time. This effect may be attributed to the use of the spacer described hereinbefore (the residue A, B or C in the cinnamic acid derivatives of formulas (1)–(3)).

Each of the cinnamic acid derivatives of formulas (1)–(3) exists generally in the trans form and when it is present at the intermolecular distance of approximately 4 Angstrom units (Å) and exposed to light of a specific wavelength of the UV region (280 nm), the derivative undergoes dimerization. However, at intermolecular distances longer than approximately 4 Å, the derivative does not dimerize and even if its molecule is excited, it isomerizes into a radiation-inert geometrical isomer, i.e. cis-form. While the cinnamic acid derivative of this invention forms a cinnamic acid-polysaccharide derivative by introduction into a polysaccharide compound, the photodimerization reaction on the chain of the introduced host polysaccharide compound, such as glycosaminoglycan, is identical, in principle, to the above-mentioned dimerization reaction. Therefore, it is important that molecules of the cinnamic acid derivative should first exist at said dimerizable intermolecular distance in the photodimerization reaction.

In this invention, the molecules of one or more cinnamic acid-polysaccharide derivatives selected from among those of formulas (13)–(15), namely molecules of mutual compound (13), mutual compound (14), mutual compound (15), compounds (13) and (14), compounds (13) and (15), compounds (14) and (15), or $R^1$ and $R^1$, $R^2$ and $R^2$, or $R^1$ and $R^2$ of compounds (13)–(15), are photodimerized to form a crosslinked cyclobutane ring and thereby provide a crosslinked cinnamic acid-polysaccharide derivative. Where photocrosslinking is to occur between compounds of the same formula for compounds of formulas (13)–(15), the concrete compounds to be submitted to the reaction may be the same compound or different compounds.

The crosslinked cyclobutane ring of the crosslinked cinnamic acid-polysaccharide derivative of this invention may generally exist as two structural isomers, namely the truxinic acid derivative and the truxillic acid derivative, and each of them may exist in a plurality of stereoisomers. The crosslinked cinnamic acid derivative of the invention may be in any of such structures.

For example, while the photocrosslinking of the cinnamic acid-polysaccharide derivative can be effected by UV irradiation after the derivative has been made into a film by the casting method, the reactivity for this photocrosslinking reaction appears to be governed by the molecular orientation obtained in the casting process.

A schematic illustration of concept of the photoreaction for the formation of the crosslinked cinnamic acid-polysaccharide derivative of this invention is presented in FIG. 1. Compared with the case in which cinnamic acid has been introduced directly into a host polysaccharide chain, the reactivity for photodimerization is enhanced by the freedom of the interposed spacer. This is not a sole factor, however, and the hydrophobicity of the spacer also has a great influence on the photoreactivity.

As such a spacer, an organic group having the structure characterized by a carbon skeleton and two or more of functional groups is exemplified. Specific examples thereof include amino acids or derivatives thereof, peptides, aminoalcohols, diamines, oligosaccharides, diols, hydroxy acids, etc. Preferable examples are amino acids and derivatives thereof, peptides and aminoalcohols.

While FIG. 1 is a schematic presentation of the photocrosslinking reaction according to this invention, in the figure reference numeral 1 indicates the cinnamic acid-polysaccharide derivative. This cinnamic acid-polysaccharide derivative 1 is a compound combined a polysaccharide compound 2 with cinnamic acid derivative, and this cinnamic acid derivative comprises a trans-cinnamic acid 4 molecule bound to a spacer 3. When this cinnamic acid-polysaccharide derivative 1 is exposed to ultraviolet radiation (UV), the photocrosslinking groups of adjacent trans-cinnamic acid molecules are bound to each other to form a cyclobutane ring and gives a dimer 6. Thus, the cinnamic acid-polysaccharide derivative 1. is converted to the crosslinked cinnamic acid-polysaccharide derivative 5. Some cinnamic acid molecules remain unreacted as cis-cinnamic acid 7 which is inert to the photocrosslinking reaction.

When a cinnamic acid derivative is introduced into a hydrophilic polysaccharide such as a glycosaminoglycan and the resulting compound is molded (e.g. cast into a film) with the elimination of water, a high hydrophobicity of the cinnamic acid derivative results in mutual attraction and aggregation of the molecules through hydrophobic binding.

Thus, the derivative tends to take a molecular orientation which favors photodimerization. Therefore, an increase in the hydrophobicity of a cinnamic acid derivative can be a factor in enhancement of the reactivity for photodimerization. The photodimerization reaction between the crosslinking groups on the cinnamic acid-polysaccharide derivative results in the construction of a three-dimensional network structure due to the crosslinked cyclobutane rings of the cinnamic acid-polysaccharide derivative. The crosslink density of such a network structure is governed by the photodimerizability of the cinnamic acid derivative. A difference in crosslink density influences on the water absorption rate and strength of the crosslinked product. Generally the higher is the crosslink density, the lower is the water absorption rate and the higher is the strength obtained. Therefore, even if such crosslinking groups are introduced into a host polysaccharide at the same degree of substitution and the resulting compound is irradiated with ultraviolet light for the same times period, differences in various physical properties are ensured according to difference of spacers. Therefore, the physical characteristics of the crosslinked cinnamic acid-polysaccharide derivative can be controlled by a judicious selection of the proper spacer as well.

The use of a glycosaminoglycan, which is a biogenic substance, as the host polysaccharide for introduction of a cinnamic acid derivative is advantageous for medical applications in the sense that the inherent characteristics of the glycosaminoglycan can be exploited and the risk of damage to the bio-body can then be virtually avoided.

Moreover, that a highly sensitive cinnamic acid derivative could be obtained by interposing a spacer has enabled the production of a crosslinked cinnamic acid-polysaccharide derivative at a low degree of substitution of crosslinking group and in a reduced UV exposure time. This implies that the physical characteristics of a crosslinked cinnamic acid-polysaccharide derivative can be controlled at a degree of substitution which is so low as to be substantially negligible in terms of the effect on bio-body. Therefore, the intrinsic properties of the host polysaccharide such as a glycosaminoglycan can be almost fully retained.

The following examples are intended to describe this invention in further detail and should by no means be construed as limiting the scope of the invention. Unless otherwise indicated herein, all parts, percents, ratios and the like are by weight.

[Synthesis of Cinnamic Acid Derivatives]In the following description, Boc means t-butoxy-carbonyl.

[1-1] EXAMPLES 1–6

Synthesis of a compound corresponding to formulas (1) and (6) as represented by the formula;

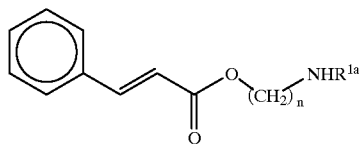

(wherein $R^1$ represents a group of the formula (4), $R^3=R^4=H$, and $R^{1a}=H$ or an amino-protecting group)

EXAMPLE 1

Synthesis of 3-Aminopropyl Cinnamate [compound (1a-1), n=3, $R^{1a}$=H] Hydrochloride 1-1: Synthesis of [compound (1-1), n=3, $R^{1a}$=Boc]

To 1.21 g (6.9 mmol) of t-butoxycarbonyl-3-amino-propanol was added 6 ml of chloroform and, then under ice-cooling, 956 μl (6.9 mmol) of triethylamine, 1.15 g (6.9 mmol) of cinnamoyl chloride, and 253 mg (2.1 mmol) of 4-dimethylaminopyridine were added successively. The mixture was stirred at room temperature for 20 minutes. This reaction mixture was diluted with ethyl acetate and washed successively twice with 5% aqueous solution of citric acid, water, 5% aqueous solution of sodium hydrogen carbonate, and with water, and a saturated aqueous solution of sodium chloride in a separatory funnel. The organic layer was dried over anhydrous sodium sulfate. The sodium sulfate was then filtered off and the filtrate was concentrated under reduced pressure. The residual white solid was washed with hexane and dried in vacuo to provide 1.38 g (yield 65%) of compound (1-1).

1-2; Synthesis of 3-aminopropyl cinnamate [compound (1a-1), n=3, $R^{1a}$=H] hydrochloride To 860 mg (2.8 mmol) of compound (1-1) was added 6 ml of 4M HCl/dioxane solution under ice-cooling and the mixture was stirred at room temperature for 35 minutes. To this reaction mixture was added ether and the resulting crystals were filtered off, washed with ether, and dried in vacuo to provide compound (1a-1) as white crystals. Yield 76%, m.p. 115.2–116.3° C.

$^1$H-NMR (400 MHz, $D_2O$):

δ (ppm)=2.16 (2H, quant, $H_2NCH_2CH_2MCH_2O$—), 3.21 (2H, t, $H_2N\underline{CH_2}CH_2CH_2$—), 4.37 (2H, t, $H_2NCH_2CH_2\underline{CH_2}O$—), 6.62 (1H, d, —CH=$\underline{CH}$CO—), 7.52 (3H, m, Aromatic H, 3,4,5 positions), 7.72 (2H, dd, Aromatic H, 2,6 positions), 7.80 (1H, d, —$\underline{CH}$=CHCO—)

EXAMPLE 2

Synthesis of 4-Aminobutyl Cinnamate [compound (1a-2), n=4, $R^{1a}$=H] Hydrochloride 2-1: Synthesis of [compound (1-2), n=4, $R^{1a}$=-Boc]

The title compound was synthesized following essentially the procedure described in Example 1-1. Yield 93%.

2-2: Synthesis of 4-aminobutyl cinnamate [compound (1a-2), n=4, $R^{1a}$=H] hydrochloride The title compound was synthesized following essentially the procedure described in Example 1-2. Yield 88%, m.p. 91.2–92.4° C.

$^1$H-NMR (400 MHz, $D_2O$):

δ (ppm)=1.85 (4H, m, $H_2NCH_2(\underline{CH_2})_2CH_2O$—), 3.10 (2H, t, $H_2N\underline{CH_2}(CH_2)_3O$—), 4.30 (2H, t, $H_2N(CH_2)_3\underline{CH_2}O$—), 6.83 (1H, d, —CH=$\underline{CH}$CO—), 7.53 (3H, m, Aromatic H, 3,4,5 positions), 7.70 (2H, dd, Aromatic H, 2,6 positions), 7.80 (1H, d, —$\underline{CH}$=CHCO—)

EXAMPLE 3

Synthesis of 5-Aminopentyl Cinnamate [compound (1a-3), n=5, $R^{1a}$=H] Hydrochloride 3-1 Synthesis of [compound (1-3), n-5, $R^{1a}$=Boc]

The title compound was synthesized following essentially the procedure described in Example 1-1. Yield 100%.

3-2: Synthesis of 5-aminopentyl cinnamate [compound (1a-3), n=5, $R^{1a}$=H] hydrochloride The title compound was synthesized following essentially the procedure described in Example 1-2. Yield 88%, m.p. 150.3–153.4° C.

$^1$H-NMR (400 MHz, $D_2O$):

δ(ppm)=1.52 (2H, quant, $H_2NCH_2CH_2\underline{CH_2}CH_2CH_2O$—), 1.70–1.86 (4H, m, $H2NCH_2\underline{CH_2}CH_2\underline{CH_2}CH_2O$—), 3.05 (2H, t, $H_2N\underline{CH_2}(CH_2)_4O$—), 4.29 (2H, t, $H_2N(CH_2)_4\underline{CH_2}O$—), 6.61 (1H, d, —CH=$\underline{CH}$CO—), 7.51 (3H, m, Aromatic H, 3,4,5 positions), 7.69 (2H, d, Aromatic H, 2,6 positions), 7.78 (1H, d, —$\underline{CH}$=CHCO—)

EXAMPLE 4

Synthesis of 6-Aminohexyl Cinnamate [compound (1a-4), n=6, $R^{1a}$=H] Hydrochloride 4-12 Synthesis of [compound (1-4), n=6, $R^{1a}$=Boc]

The title compound was synthesized following essentially the procedure described in Example 1-1. Yield 99%.

4-2; Synthesis of 6-aminohexyl cinnamate [compound (1a-4), n=6, $R^{1a}$=H] hydrochloride The title compound was synthesized following essentially the procedure described in Example 1-2. Yield 86%, m.p. 98.8–100.4° C.

$^1$H-NMR (400 MHz, $D_2O$):

δ (ppm)=1.48–1.53 (4H, m, $H_2NCH_2CH_2$($\underline{CH_2}$)$_2CH_2CH_2O$—), 1.63–1.83 (4H, m, $H_2NCH_2$$\underline{CH_2}$(CH$_2$)$_2$$\underline{CH_2}$CH$_2$O—), 3.02 (2H, t, $H_2N$$\underline{CH_2}$(CH$_2$)$_5$O—), 4.28 (2H, t, $H_2N(CH_2)_5\underline{CH_2}O$—), 6.60 (1H, d, —CH=$\underline{CH}$CO—), 7.53 (3H, m, Aromatic H, 3,4,5 positions), 7.68 (2H, d, Aromatic H, 2,6 positions), 7.76 (1H, d, —$\underline{CH}$=CHCO—)

EXAMPLE 5

Synthesis of 8-Aminooctyl Cinnamate [compound (1a-5), n=8, $R^{1a}$=H] Hydrochloride 5-1; Synthesis of [compound (1-5), n=8, $R^{1a}$=Boc]

The title compound was synthesized following essentially the procedure described in Example 1-1. Yield 87%.

5-2: Synthesis of 8-aminooctyl cinnamate [compound (1a-5), n=8, $R^{1a}$=H] hydrochloride The title compound was synthesized following essentially the procedure described in Example 1-2. Yield 88%, m.p. 86.5–87.3° C.

$^1$H-NMR (400 MHz, $D_2O$)

δ (ppm)=1.31–1.48 (8H, m, $H_2NCH_2CH_2$($\underline{CH_2}$)$_4CH_2CH_2O$—), 1.62–1.79 (4H, m, $H_2NCH_2$$\underline{CH_2}$(CH$_2$)$_4$$\underline{CH_2}$CH$_2$O—), 2.99 (2H, t, $H_2N$$\underline{CH_2}$(CH$_2$)$_7$O—), 4.26 (2H, t, $H_2N(CH_2)_7\underline{CH_2}O$—), 6.58 (1H, d, —CH=$\underline{CH}$CO—), 7.52 (3H, m, Aromatic H, 3,4,5 positions), 7.68 (2H, d, Aromatic H, 2,6 positions), 7.76 (1H, d, —$\underline{CH}$=CHCO—)

EXAMPLE 6

Synthesis of 12-Aminododecyl Cinnamate [compound (1a-6), n=12, $R^{1a}$=H] Hydrochloride 6-1: Synthesis of [compound (1-6), n=12, $R^{1a}$=Boc]

The title compound was synthesized following essentially the procedure described in Example 1-1. Yield ca 100%.

6-2; Synthesis of 12-aminododecyl cinnamate [compound (1a-6), n=12, $R^{1a}$=H] hydrochloride The title compound was synthesized following essentially the procedure described in Example 1-2. Yield 82%, m.p. 90.7–93.1° C.

$^1$H-NMR (400 MHz, $D_2O$):

δ (ppm)=1.24–1.50 (16H, m, $H_2NCH_2CH_2$($\underline{CH_2}$)$_8CH_2CH_2O$—), 1.64 (2H, quant, $H_2NCH_2$$\underline{CH_2}$(CH$_2$)$_{10}$O—), 1.76 (2H, quant, $H_2N(CH_2)_{10}$$\underline{CH_2}$CH$_2$O—), 2.96 (2H, t, $H_2N\underline{CH_2}(CH_2)_{11}O$—), 4.28 (2H, t, $H_2N(CH_2)_{11}\underline{CH_2}O$—), 6.61 (1H, d, —CH=$\underline{CH}$CO—), 7.53 (3H, m, Aromatic H, 3,4,5 positions), 7.68 (2H, d, Aromatic H, 2,6 positions), 7.76 (1H, d, —$\underline{CH}$=CHCO—)

[1-2] Synthesis of a compound corresponding to formulas (1) and (7) as represented by the formula:

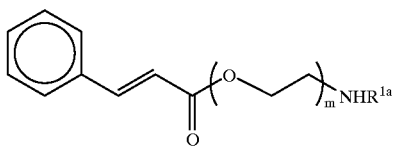

(wherein $R^1$ represents a group of the formula (4), $R^3$=$R^4$=H)

EXAMPLE 7

Synthesis of 2-(2-Aminoethoxy)ethyl Cinnamate [compound (1a-7), m=2, $R^{1a}$=H] Hydrochloride 7-1: Synthesis of [compound (1-7), m=2, $R^{1a}$=Boc]

Using Boc-NH(CH$_2$CH$_2$O)$_2$H in lieu of Boc-NH(CH$_2$)$_3$OH, the title compound was synthesized following essentially the procedure described in Example 1-1. Yield 85%.

7-2; Synthesis of 2-(2-aminoethoxy)ethyl cinnamate [compound (1a-7), m=2, $R^{1a}$=H) hydrochloride Using compound (1-7) in lieu of compound (1-1), the title compound was synthesized following essentially the procedure described in Example 1-2. Yield ca 100%, m.p. 80.8–82.5° C.

$^1$H-NMR (400 MHz, $D_2O$):

δ (ppm)=3.26 (2H, t, $H_2\underline{CH_2}CH_2O$—), 3.94 (2H, t, $H_2NCH_2\underline{CH_2}O$—), 3.88 (2H, t, —O$\underline{CH_2}$CH$_2$OCO—), 4.40 (2H, t, —O$\underline{CH_2}$CH$_2$OCO—), 6.54 (1H, d, —CH=$\underline{CH}$CO—), 7.49 (3H, m, Aromatic H, 3,4,5 positions), 7.64 (2H, m, Aromatic H, 2,6 positions), 7.73 (1H, d, —$\underline{CH}$=CHCO—)

[1-3] Synthesis of a compound corresponding to formulas (1) and (9) as represented by the formula

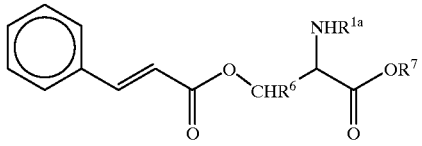

(wherein $R^1$ represents a group of the formula (4), $R^3$=$R^4$=H; and in the formula (8), $R^6$=H, $R^7$=CH$_3$)

EXAMPLE 8

Synthesis of O-Cinnamoyl Serine Methyl Ester [compound (1a-8), $R^{1a}$=H] Hydrochloride 8-1: Synthesis of [compound (1-8), $R^{1a}$=Boc]

In 9 ml of chloroform was dissolved 1.93 g (8.8 mmol) of t-butoxycarbonylserine methyl ester and, then under ice-cooling, a solution of 2.94 g (10.6 mmol) of cinnamic acid anhydride in 10 ml chloroform, 1.46 ml (10.6 mmol) of triethylamine, and a solution of 645 mg (4.4 mmol) of 4-dimethylaminopyridine in 2 ml chloroform were added successively. The mixture was stirred at room temperature for 35 minutes and, then, concentrated under reduced pressure to reduce liquid volume. This solution was diluted with ethyl acetate and washed successively twice with 5% citric acid, once with water, twice with a 5% aqueous solution of sodium hydrogen carbonate, once with water, and twice with a saturated aqueous solution of sodium chloride. The organic layer was dried over anhydrous sodium sulfate for 1 hour. The sodium sulfate was then filtered off and the filtrate was concentrated under reduced pressure. To the residue was added ether and the resulting crystal crop was recrystallized from ethyl acetate-petroleum ether to provide 2.10 g (yield 68%) of white crystals of compound (1-8).

Structure was confirmed by $^1$H-NMR.
$^1$H-NMR (400 MHz, CDCl$_3$):

δ (ppm)=1.45 (9H, s, Boc-), 3.80 (3H, s, —COOCH$_3$), 4.51 (2H, dd, β—CH$_2$), 4.65 (1H, br, α—CH), 5.38 (1H, br, CONH), 6.40 (1H, d, PhCH=C<u>H</u>—), 7.45 (5H, m, Ph—), 7.70 (1H, 8, PhC<u>H</u>=CH—)

8-2: Synthesis of O-cinnamoyl serine methyl ester [compound (1a-8), R$^{1a}$=H] hydrochloride Under ice-cooling, trifluoroacetic acid was added to 1.48 g (4.2 mmol) of compound (1-8) up to the level where the crystals were fully immersed and the mixture was allowed to stand for 30 minutes. Then, 1.1 ml of 4M HCl/dioxane solution was added. After crystallization by addition of hexane, the crystal crop was filtered off and washed with ether-hexane on a glass filter to provide 1.39 g (yield 91%) of compound (1a-8) as white crystals. m.p. 144.5–147.0° C.

$^1$H-NNR (400 MHz, D$_2$O):

δ (ppm)=3.92 (3H, s, —COOCH$_3$), 4.58–4.75 (3H, dd, Ser α—H, β—H), 6.80 (1H, d, —CH=C<u>H</u>CO—), 7.50 (3H, m, Aromatic H, 3,4,5 positions), 7.69 (2H, d, Aromatic H, 2,6 positions), 7.82 (1H, d, —C<u>H</u>=CHCO—)

[1-4] Examples 9-11: Synthesis of a compound corresponding to formulas (1) and (9) as represented by the following formula

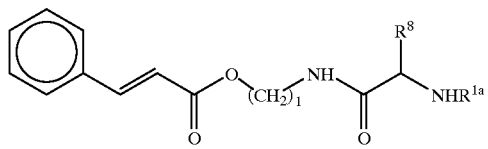

(wherein R$^1$ represents a group of the formula (4), R$^3$=R$^4$=H)

EXAMPLE 9

Synthesis of [compound (1a-9), l=2, R$^{1a}$=H, R$^8$=H] Hydrochloride

In 2 ml of chloroform was dissolved 175 mg (1.0 mmol) of t-butoxycarbonylglycine and, then under ice-cooling, 139 μl (1.0 mmol) of triethylamine and 1.0 ml (1.0 mmol) of 1M dimethylphosphinothioyl chloride/chloroform solution were added. The mixture was stirred at room temperature for 20 minutes. Then, 139 μl (1.0 mmol) of triethylamine and a previously prepared solution of 2-aminoethyl cinnamate hydrochloride (1.0 mmol) and 139 μl (1.0 mmol) triethylamine in 2 ml of chloroform were added under ice-cooling and the mixture was stirred at room temperature for 2 hours. After completion of the reaction, 4 ml of methanol and 1 ml of aqueous ammonia were added and the mixture was stirred for 30 minutes. This solution was once concentrated under reduced pressure once and the residue was diluted with ethyl acetate and washed successively twice with water, a 5% aqueous sodium hydrogen carbonate solution, water, a 5% aqueous citric acid solution, and with water, and a saturated aqueous sodium chloride solution. The organic layer was dried over anhydrous sodium sulfate and concentrated under reduced pressure to provide [compound (1-9), l=2, R$^{1a}$=Boc, R$^8$=H]. To this compound was added 3 ml of 4M HCl/dioxane solution under ice-cooling, and the mixture was stirred at room temperature for 30 minutes and concentrated under reduced pressure to provide 106 mg (yield 35%) of the objective compound (1a-9) as white solid. m.p. 162.5–165.8° C.

$^1$H-NMR (400 MHz, D$_2$O):

δ (ppm)=3.83 (2H, s, —NHC<u>H</u>$_2$CO—), 3.66 (2H, t, —NHC<u>H</u>$_2$CH$_2$O—, 4.38 (2H, t, —NHCH$_2$C<u>H</u>$_2$O—), 6.62 (1H, d, —CH=C<u>H</u>CO—), 7.53 (3H, m, Aromatic H, 3,4,5 positions), 7.70 (2H, d, Aromatic H, 2,6 positions), 7.81 (1H, d, —C<u>H</u>=CHCO—)

EXAMPLE 10

Synthesis of [compound (1a-1), l=2, R$^{1a}$=H, R$^8$=CH$_3$] Hydrochloride

Using t-butoxycarbonylalanine in lieu of t-butoxycarbonylglycine, the title compound was synthesized following essentially the procedure described in Example 9. Yield 45%.

$^1$H-NMR (400 MHz, D$_2$O):

δ (ppm)=2.53 (3H, d, —CH$_3$), 3.55 (1H, dt, —NH C<u>H</u>$_2$CH$_2$O—), 3.72 (1H, dt, —NHC<u>H</u>$_2$CH$_2$O—), 4.08 (1H, qualt, Ala α—H), 4.36 (2H, t, —NHCH$_2$ C<u>H</u>$_2$O—), 6.58 (1H, d, —CH=C<u>H</u>CO—), 7.50 (3H, m, Aromatic H, 3,4,5 positions), 7.67 (2H, d, Aromatic H, 2,6 positions), 7.76 (1H, d, —C<u>H</u>=CHCO—)

EXAMPLE 11

Synthesis of [compound (1a-11), l=2, R$^{1a}$=H, R$^8$=(CH$_3$)$_2$CHCH$_2$—] Hydrochloride Using t-butoxycarbonylleucine in lieu of t-butoxycarbonylglycine, the title compound was synthesized following essentially the procedure described in Example 9. Yield 58%.

$^1$H-NMR (400 MHz, D$_2$O):

δ (ppm)=0.90 (6H, dd, —CH(C<u>H</u>$_3$)$_2$), 1.55–1.80 (3H, m, —CH$_2$CH(CH$_3$)$_2$), 3.44 (1H, dt, —NHC<u>H</u>CH$_2$O—), 3.88 (1H, dt, —NHC<u>H</u>$_2$CH$_2$O—), 3.99 (1H, t, Leu α-H), 4.39 (2H, t, —NHCH$_2$C<u>H</u>$_2$O—), 6.60 (1H, d, —CH=C<u>H</u>CO—), 7.51 (3H, m, Aromatic H, 3,4,5 positions), 7.70 (2H, d, Aromatic H, 2,6 positions), 7.78 (1H, d, —C<u>H</u>=CHCO—)

[2] Examples 12–15: Synthesis of a compound corresponding to formulas (2) and (10) as represented by the following formula

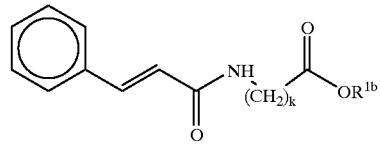

(wherein R$^1$ represents a group of the formula (4), R$^3$=R$^4$=H)

EXAMPLE 12

Synthesis of Cinnamoylglycine [compound (2-1), k=1, R$^{1b}$=H]

12-1: Cinnamoylglycine methyl ester [compound (2-1b), k=1, R$^{1b}$=CH$_3$]

In 10 ml of chloroform was suspended 1.26 g (10 mmol) of glycine methyl ester hydrochloride and, under ice-cooling, 2.77 ml (20 mmol) of triethylamine and 10 ml of 2.78 g (10 mmol) of cinnamic acid anhydride/chloroform were successively added. The mixture was stirred at room temperature for 24 hours. The reaction mixture was then diluted with 50 ml of ethyl acetate and washed successively twice with a 5% aqueous citric acid solution, water, a 5% aqueous sodium hydrogen carbonate solution, and with water, and a saturated aqueous sodium chloride solution. The organic layer was dried over anhydrous sodium sulfate. The sodium sulfate was filtered off and the filtrate was concentrated under reduced pressure. The residue was recrystallized from ethyl acetate-petroleum ether to provide 1.67 g (yield 71%) of compound (2-lb) as platelets. Structure was confirmed by $^1$H-NMR.

$^1$H-NMR (400 MHz, CDCl$_3$):

δ (ppm)=3.80 (3H, 9, —OCH$_3$), 4.20 (2H, s, —NH CH$_2$CO—), 6.15 (1H, br, —CONH—), 6.45 (1H, d, —CH═CHCO), 7.45 (5H, dd, Aromatic H), 7.75 (1H, d, —CH═CHCO—)

12-2: Synthesis of cinnamoylglycine [compound (2-1), k=1, R$^{1b}$=H]

In 10 ml of methanol was dissolved 402 mg (1.7 mmol) of compound (2-1b) and, under ice-cooling, 468 μl (1.87 mmcol) of 4M aqueous sodium hydroxide solution was added. The mixture was stirred at room temperature for 24 hours. This reaction mixture was concentrated under reduced pressure, and after addition of chloroform and water, the objective compound was extracted into the aqueous phase. To the aqueous phase was added citric acid until the solution became acidic, followed by extraction three times with ethyl acetate. The extracted organic layer was pooled and washed with saturated aqueous sodium chloride solution, and the organic layer was dried over anhydrous sodium sulfate. The sodium sulfate was filtered off and the filtrate was concentrated under reduced pressure. The resulting crystals were washed with ether on a glass filter and dried in vacuo to provide 324 mg (yield 86%) of compound (2-1). m.p. 194.7–197.3° C.

$^1$H-NMR (400 MHz, CDCl$_3$-DMSO):

δ (ppm)=4.11 (2H, dd, —NHCH$_2$CO), 6.60 (1H, dd, —CH═CHCO—), 7.05 (1H, br, —CONH—), 7.37 (3H, m, Aromatic H, 3,4,5 positions), 7.52 (2H, dd, Aromatic H, 2,6 positions), 7.61 (1H, d, —CH═CHCO—)

EXAMPLE 13

Synthesis of Cinnamoyl-β-alanine [compound (2-2), k=2, R$^{1b}$=H]

13-1; Synthesis of cinnamoyl-β-alanine ethyl ester [compound (2-2b), k=2, R$^{1b}$=C$_2$H$_5$]

Using β-alanine ethyl ester hydrochloride in lieu of glycine methyl ester hydrochloride, the title compound was synthsized following essentially the procedure described in Example 12-1. Yield 58%.

13-2; Synthesis of cinnamoyl-β-alanine [compound (2-2), k=2, R$^{1b}$=H]

Using compound (2-2b) in lieu of compound (2-1b), the title compound was synthesized following essentially the procedure described in Example 12-2. Yield 65%, m.p. 140.2–143.7° C.

$^1$H-NXR (400 MHz, CDCl$_3$-DMSO):

δ (ppm)=2.78 (2H, t, —NHCH$_2$CH$_2$CO—), 3.63 (2H, dd, —NHCH$_2$CH$_2$CO—), 6.43 (1H, d, —CH═CHCO—), 6.80 (1H, br, CONH), 7.35 (3H, m, Aromatic H. 3,4,5 positions), 7.50 (2H, d, Aromatic H, 2,6 positions), 7.59 (1H, d, —CH═CHCO—)

EXAMPLE 14

Synthesis of Cinnamoyl-γ-aminobutyric Acid [compound (2-3), k=3, R$^{1b}$=H]

In 2 ml of water was dissolved 1.03 g (10 mmol) of γ-aminobutyric acid and, under ice-cooling, 2.5 ml of 4M aqueous sodium hydroxide solution and 3 ml of 1.58 ml cinnamoyl chloride/dioxane solution were added dropwise each in 3 portions so that the mixture would be maintained under alkaline conditions. After completion of dropwise addition, the reaction mixture was stirred at room temperature for 24 hours and the dioxane was then distilled off under reduced pressure. The resulting aqueous solution was washed with ethyl acetate twice to remove the starting material. This aqueous solution was acidified with citric acid and the objective compound was extracted into ethyl acetate. The organic layer was dried over anhydrous sodium sulfate. The solution free from the sodium sulfate was concentrated under reduced pressure to give a crystal crop. This crystal crop was recrystallized from ethanol/ether/hexane to provide 1.98 g (yield 85%) of compound (2-3) as white crystals. m.p. 82.2–83.6° C.

$^1$H-NMR (400 MHz, CDCl$_3$):

δ (ppm)=1.93 (2H, quant, —NHCH$_2$CH$_2$CH$_2$CO—), 2.45 (2H, t, —NHCH$_2$CH$_2$CH$_2$CO—), 3.48 (2H, qualt, —NHCH$_2$CH$_2$CH$_2$CO—), 5.97 (1H, br, CONH), 6.40 (1H, d, —CH═CHCO—), 7.33 (3H, m, Aromatic, H 3,4,5 positions), 7.49 (2H, d, Aromatic H, 2,6 positions), 7.64 (1H, d, —CH═CHCO—)

EXAMPLE 15

Synthesis of Cinnamoyl-6-aminocaproic Acid [compound (2-4), k=5, R$^{1b}$=H]

Using 6-aminocaproic acid in lieu of γ-aminobutyric acid, the title compound was synthesized following essentially the procedure described in Example 14. Yield 77%, m.p. 91.6–92.3° C.

$^1$H-NMR(400 MHz, CDCl$_3$):

δ (ppm)=1.44 (2H, quant, —NHCH$_2$CH$_2$CH$_2$CH$_2$CH$_2$CO—), 1.61 (2H, quant, —NHCH$_2$CH$_2$CH$_2$CH$_2$CO—), 1.69 (2H, quant, —NHCH$_2$CH$_2$CH$_2$CH$_2$CH$_2$CO—), 2.38 (2H, t, —NH(CH$_2$)$_4$CH$_2$CO—), 3.40 (2H, qualt, —NHCH$_2$(CH$_2$)$_4$CO—), 5.68 (1H, br, CONH), 6.37 (1H, d, —CH═CHCO—), 7.35 (3H, m, Aromatic H, 3,4,5 positions), 7.48 (2H, d, Aromatic H, 2,6 positions), 7.61 (1H, d, —CH—CHCO—)

[3-1] Examples 16-18: Synthesis of a compound corresponding to formulas (3) and (11) as represented by the formula:

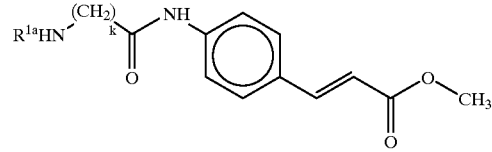

(wherein R$^2$ represents a group of the formula (3), and in the formula (5), R$^3$=R$^4$=H, R$^5$=CH$_3$)

EXAMPLE 16

Synthesis of Methyl 4-(4-Aminobutyrylamino cinnamate Hydrochloride [compound (3a-1), k=3, R$^{1a}$=H]

16-1: Synthesis of [compound (3-1), k=3, R$^{1a}$=Boc]

In 3 ml of chloroform was dissolved 2.02 g (10 mmol) of t-butoxycarbonyl-γ-aminobutyric acid and, under ice-cooling, 1.38 ml (10 mmol) of triethylamine and 1.28 g (10 mmol) of dimethylphosphinothioyl chloride were successively added. The mixture was stirred at room temperature for 10 minutes. Under ice-cooling, 532 mg (3 mmol) of methyl p-aminocinnamate hydrochloride and 3 ml of a solution of 417 μl (3 mmol) of triethylamine in chloroform were added, followed by addition of a further 417 μl (3 mmol) of triethylamine. The mixture was stirred at room temperature for 24 hours. After completion of the reaction, the chloroform was distilled off under reduced pressure and the residue was diluted with ethyl acetate and washed successively twice with a 5% aqueous citric acid solution, water, a 5% aqueous sodium hydrogen carbonate solution, and with water, and a saturated aqueous sodium chloride solution in a separatory funnel. The organic layer was dried over anhydrous sodium sulfate.

The sodium sulfate was then filtered off and the filtrate was dried in vacuo to provide 483 mg (yield 44%) of compound (3-1).

16-2: Synthesis of methyl 4-(4-aminobutrylamino)cinnamate hydrochloride [compound (3a-1), k=3, $R^{1a}$=H]

To 409 mg (1.13 mmol) of compound (3-1) was added 4 ml of 4N-HCl/dioxane solution under ice-cooling, and the mixture was stirred at room temperature for 30 minutes. After completion of the reaction, 90 ml of anhydrous ether was added and the resulting precipitate was filtered using a glass filter and washed 2 or 3 times with ether. The resulting solid was dried in vacuo to provide compound (3a-1) as white solid. Yield 92%, m.p. 206.0–208.0° C.

$^1$H-NMR (400 MHz, $D_2O$):

δ (ppm)=2.07 (2H, quant, $H_2NCH_2\underline{CH_2}CH_2CO$—), 2.62 (2H, t, $H_2NCH_2CH_2\underline{CH_2}CO$—), 3.10 (2H, t, $H_2N\underline{CH_2}CH_2CH_2CO$—), 3.82 (3H, s, —$COCH_3$), 6.53 (1H, m, —CH═$\underline{CH}CO$—), 7.53 (2H, m, Aromatic H, 2,6 positions), 7.58–7.76 (3H, m, Aromatic H, 3,5 positions, —$\underline{CH}CHCO$—)

EXAMPLE 17
Synthesis of Methyl 4-(6-Aminohexanoylamino)cinnamate Hydrochloride [compound (3a-2), k=5, $R^{1a}$=H]

17-1: Synthesis of [compound (3-2), k=5, $R^{1a}$=Boc]

The procedure of Example 16-1 was generally repeated to synthesize the title compound. Yield 40%.

17-2: Synthesis of methyl 4-(6-aminohexanoylamino)cinnamate hydrochloride [compound (3a-2), k=5, $R^{1a}$=H]

The title compound was synthesized following essentially the procedure described in Example 16-2. Yield 97%, m.p. 215.4–219.6° C.

$^1$H-NMR (400MHz, $D_2O$):

δ (ppm)=1.47 (2H, quant, $H_2NCH_2CH_2\underline{CH_2}CH_2CH_2CO$—), 1.72 (4H, m, $H_2NCH_2\underline{CH_2}CH_2\underline{CH_2}CH_2CO$—), 2.48 (2H, t, $H_2NCH_2CH_2CH_2CH_2\underline{CH}CH_2CO$—), 3.03 (2H, t, $H_2N\underline{CH_2}CH_2CH_2CH_2CH_2CO$—), 3.82 (3H, e, —$COOCH_3$), 6.53 (1H, m, —CH═$\underline{CH}CO$—), 7.51 (2H, d, Aromatic H, 2,6 positions), 7.61–7.76 (3H, m, Aromatic H, 3,5 positions, —$\underline{CH}$═CHCO—)

EXAMPLE 18
Synthesis of Methyl 4-(12-Aminododecanoylamino)cinnamate [compound (3a-3), k=1, $R^{1a}$=H] Hydrochloride 18-1: Synthesis of [compound (3-3), k=11, $R^{1a}$=Boc]

The title compound was synthesized following essentially the procedure described in Example 16-1. Yield 72%.

18-2s Synthesis of methyl 4-(12-aminododecanoylamino)cinnamate [compound (3a-3), k=11, $R^{1a}$=H] hydrochloride The title compound was synthesized following essentially the procedure described in Example 16-2. Yield 94%, m.p. 210.2–217.0° C.

$^1$H-NMR (400 MHz, $CDCl_3$-$DMSO$-$D_2O$);

δ (ppm)=1.20–1.38 (14H, m, $H_2NCH_2CH_2(\underline{CH_2})_7CH_2CH_2CO$—), 1.53–1.69 (4H, m, $H_2NCH_2\underline{CH_2}(CH_2)_7\underline{CH_2}CH_2CO$—), 2.34 (2H, t, $H_2N(CH_2)_{10}\underline{CH_2}CO$—), 2.80 (2H, t, $H_2N\underline{CH_2}(CH_2)_{10}CO$—), 3.73 (3H, s, —$COOCH_3$), 6.38 (1H, d, —CH═$\underline{CH}CO$—), 7.52 (2H, d, Aromatic H. 2,6 positions), 7.58 (1H, d, —$\underline{CH}$═CHCO—), 7.68 (2H, m, Aromatic H, 3,5 positions)

[3-2] Examples 19-21; Synthesis of a compound corresponding to formulas (3) and (12) as represented by the formula:

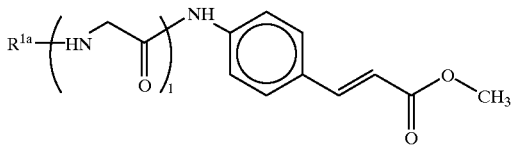

(wherein $R^2$ represents a group of the formula (3), and in the formula (5), $R^3$═$R^4$═H, $R^3$═$CH_3$; and in the formula (12), $R^8$═H)

EXAMPLE 19
Synthesis of Methyl Glycylaminocinnamate [compound (3a-4). i=1, $R^{1a}$=H] Hydrochloride 19-1: Synthesis of [compound (3-4), i=1, $R^{1a}$=Boc]

Using t-butoxycarbonylglycine in lieu of t-butoxycarbonyl-γ-aminobutyric acid, the title compound was synthesized following essentially the procedure described in Example 16-1. Yield 73%.

19-2: Synthesis of methyl glycylaminocinnamate [compound (3a-4), i-1, $R^{1a}$=H] hydrochloride Using compound (3-4) in lieu of compound (3-1), the title compound (3a-4) was synthesized following essentially the procedure described in Example 16-2. Yield of 98%. m.p. 218.6–225.6° C.

$^1$H-NMR (400 MHz, $D_2O$):

δ (ppm)=3.86 (3H, s, —$COOCH_3$), 4.02 (2H, a, Gly α—H), 6.63 (1H, d, —CH═$\underline{CH}CO$—), 7.66 (2H, m, Aromatic H, 2,6 positions), 7.75 (2H, m, Aromatic H, 3,5 positions, —$\underline{CH}$═CHCO—)

EXAMPLE 20
Synthesis of Methyl Glycylglycylaminocinnamate [compound (3a-5), i=2, $R^{1a}$=H] Hydrochloride 20-1: Synthesis of [compound (3-5), i=2, $R^{1a}$=Boc]

In 3 ml of chloroform was dissolved 526 mg (3 mmol) of t-butoxycarbonylglycine and, under ice-cooling, 416 μl (3 mmol) of triethylamine and 1 ml of a solution of 386 mg (3 mmol) dimethylphosphinothioyl chloride in chloroform were added successively. The mixture was stirred at room temperature for 15 minutes, after which 416 μl (3 mmol) of triethylamine and 10 ml of a previously prepared solution of 812 mg (3 mmol) of compound (3a-4) and 416 μl (3 mmol) of triethylamine in chloroform was added under ice-cooling, and the mixture was stirred at room temperature for 20 minutes. This reaction mixture was concentrated under reduced pressure and the residue wag diluted with ethyl acetate and washed successively twice with a 5% aqueous citric acid solution, water, a 5% aqueous sodium hydrogen carbonate solution, and with water, and a saturated aqueous sodium chloride solution. The organic layer was dried over anhydrous sodium sulfate. The sodium sulfate was filtered off and the filtrate was concentrated under reduced pressure. The resulting white crystals were washed with ether and dried in vacuo to provide 986 mg (yield 84%) of compound (3-5). Structure was confirmed by the $^1$H-NMR.

$^1$H-NMR (400 MHz, $CDCl_3$);

δ (ppm)=1.45 (9H, a, Boc-), 3.80 (3H, B, —$COOCH_3$), 3.85 (2H, a, BocGly α—H), 4.15 (2H, s, GlyGly-α—H), 5.15 (1H, br, BocNH—), 6.40 (1H, d, —CH═$\underline{CH}CO$—), 7.55 (4H, dd, Aromatic H), 7.65 (1H, d, —$\underline{CH}$═CHCO—), 8.55 (1H, br, Gly$\underline{NH}$Ar—) 20-2: Synthesis of methyl glycylglycylaminocinnamate (compound (3a-5), i=2, $R^{1a}$=HJ hydrochloride To 543 mg (1.4 mmol) of compound (3-5) was added 4 ml of 4M HCl/dioxane under ice-cooling and the mixture was stirred for 40 minutes. To this mixture was added ether and the resulting crystals were filtered and washed with ether. This crystal crop was dried in vacuo to provide 199 mg (yield 61%) of compound (3a-5) as white crystals. m.p. 219.3–231.0° C. $^1$H-NMR (400 MHz, $D_2O$):

δ(ppm)=3.83 (3H, s, —$COOCH_3$), 3.94 (2H, s, Gly<u>Gly</u>-α-H), 4.19 (2H, s, Gly<u>Gly</u>- α-H), 6.54 (1H, d, —CH=<u>CH</u>CO—), 7.54 (2H, d, Aromatic H. 2,6 positions), 7.68 (2H, d, Aromatic H, 3,5 positions), 7.73 (1H, d, —<u>CH</u>=CHCO—)

EXAMPLE 21

Synthesis of Methyl Triglycylaminocinnamate [compound (3a-6), i=3, $R^{1a}$=H] Hydrochloride 21-1: Synthesis of [compound (3-6), i=3, $R^{1a}$=Boc]

In 1 ml of dioxane was dissolved 88 mg (0.5 mmol) of t-butoxycarbonylglycine and, under ice-cooling, 69.5 μl (0.5 mmol) of triethylamine and 1 ml of a solution of 64 mg (0.5 mmol) dimethylphosphinothioyl chloride in dioxane were added successively. The mixture was stirred at room temperature for 25 minutes. Then, 69.5 μl (0.5 mmol) of triethylamine and 1 ml of a previously prepared solution of 163 mg (0.5 mmol) of compound (3a-5) and 69.5 μl (0.5 mmol) of triethylamine in dioxane were added under ice-cooling and the mixture was stirred at room temperature for 1 hour. To this reaction mixture was added 1 ml of aqueous ammonia, followed by stirring for 20 minutes. This solution was concentrated under reduced pressure and the residue was diluted with ethyl acetate and washed successively twice with a 5% aqueous citric acid solution, water, a 5% aqueous sodium hydrogen carbonate solution, and with water, and saturated aqueous sodium chloride solution. The organic layer was dried over anhydrous sodium sulfate. The sodium sulfate was then filtered off and the filtrate was concentrated under reduced pressure. The resulting white crystal crop was washed with ether and dried in vacuo to provide 153 mg (yield 89%) of compound (3-6).

21-2: Synthesis of methyl triglycylaminocinnamate [compound (3a-6), i=3, $R^{1a}$=H] hydrochloride To 137 mg (0.4 mmol) of compound (3-6) was added 3 ml of 4M HCl/dioxane under ice-cooling and the mixture was stirred for 2 hours. To this reaction mixture was added ether and the resulting crystals were collected by filtration and washed with ether. This crystal crop was dried in vacuo to provide 110 mg (yield 98%) of compound (3a-6) as white crystals. m.p. 227.3–235.8° C.

$^1$H-NMR (400 MHz, $D_2O$):

δ(ppm)=3.83 (3H, s, —$COOCH_3$), 3.94 (2H, s, <u>Gly</u>GlyGly-α-H), 4.12 (2H, s, Gly<u>Gly</u>Gly- α-H), 4.14 (2H, s, GlyGly<u>Gly</u>- α-H), 6.54 (1H, dd, —CH=CHCO—), 7.55 (2H, d, Aromatic H, 2,6 positions), 7.66 (2H, d, Aromatic H, 3,5 positions), 7.72 (1H, dd, —<u>CH</u>=CHCO—) [Synthesis of cinnamic acid-polysaccharide derivatives and crosslinked cinnamic acid-polysaccharide derivatives)

The cinnamic acid-polysaccharide derivative of this invention prior to UV irradiation is molded in shape of film suitable for UV irradiation (this film is referred to as the photocurable film) and the crosolinked cinnamic acid-polysaccharide after UV irradiation is referred to as the cured film. The degree of gelation mentioned in the examples was calculated by the following equation.

Degree of gelation (%)=(re-dry weight of film/dry weight of film)×100 where re-dry weight of the film=the weight found by immersing the film in 10,000 parts by volume of water for 24 hours at room temperature, recovering the film by filtration, drying it in vacuo, and weighing the dried film;

dry weight of the film=the weight found by drying the film in vacuo prior to wetting and weighing the dried film.

The degree of cinnamic acid derivative substitution, or DS (degree of substitution), was calculated from the molar ratio of the cinnamic acid derivative introduced per disaccharide unit of hyaluronic acid or chondroitin sulfate based on NXR or absorbance data by the following equation.

DS (%)=100×(the number of moles of cinnamic acid derivative introduced per constituent disaccharide unit)

EXAMPLES 22–32

The cinnamic acid-polysaccharide derivatives of formula (13) and the corresponding crosslinked cinnamic acid-polyeacharide derivatives, in which $P^1$ represents hyaluronic acid.

EXAMPLE 22

22-1: Preparation of a photocurable film incorporated with compound (1a-1) [compound (1a-1-HA)]

In 60 ml of water was dissolved 400 mg (1.0 mmol disaccharide unit) of a hyaluronic acid with an average molecular weight of 800,000, followed by addition of 30 ml of 1,4-dioxane. Under ice-cooling, 300 μl of 0.2 M aqueous solution of N-hydroxysuccinimide and 300 l of 0.1 M aqueous solution of a water-soluble carbodiimide were successively added and, after 5 minutes of stirring, 300 μl of 0.1 M aqueous solution of compound (1a-1) was added. After the mixture was stirred at room temperature for 4 hours, and then 350 ml of saturated sodium acetate/ethanol solution was added so as to precipitate the objective compound. The precipitate was separated by centrifugation (2500 rpm×5 min.). The sediment was washed three times with 80% ethanol and dissolved in 175 ml of water. The solution was cast in 2 square-well dishes (each, 90 mm×62 mm) and dried in an oven at 45° C. to provide samples of a film. Yield 350 mg. The film had a DS of 0.58% as determined by its absorbance. 22-2; Preparation of a cured film by UV crosslinking of the photocurable film [compound (1a-1-HA)]

The film prepared in Example 22-1 was sandwiched between a pair of 2.4 mm-thick Pyrex glass sheets and irradiated from either side with ultraviolet light using a UV irradiator (light source: a 3 kW metal halide lamp, irradiation distance 125 mm, conveyer speed 1 m/min., wavelength 250–450 nm) for 4 minutes each side or a total of 8 minutes.

Degree of gelation: 107%

EXAMPLES 23–28-and 30–32

Using the cinnamic acid derivatives listed in Table 1 shown below, photocurable films and cured films were prepared in accordance with the procedure of Example 22.

EXAMPLE 29

29-1: Preparation of a photocurable film [compound (1a-8-HA)] incorporated with compound (1a-8)

In 50 ml of water was dissolved 200 mg (0.5 mmol disaccharide unit) of a hyaluronic acid with an average molecular weight of 800,000, followed by addition of 10 ml of 1,4-dioxane. Under ice-cooling, 200 μl of 0.5 M N-hydroxysuccinimide/dioxane solution and 200 μl of 0.25 M water-soluble carbodiimide/aqueous solution were successively added. The mixture was stirred for 5 minutes and 1 ml of an aqueous solution of 14 mg (0.05 mmol) of compound (1a-8) was added. After the mixture was stirred at room temperature for 2 hours, 350 ml of saturated sodium acetate/ethanol solution was added so as to precipitate the objective compound. The precipitate was separated by centrifugation (2500 rpm×5 min.). The sediment was washed three times with a mixture of water-ethanol and dissolved in 80 ml of water. The solution was cast in a square-well dish (90 mm×62 mm) and dried in an oven at 45° C. to provide a film. Yield 201 mg. The film had a DS of 0.7% as determined by its absorbance. 29-2: Preparation of a cured film by UV crosslinking of the photocurable film [compound (1a-8-HA)]

The film prepared in Example 29-1 was sandwiched between a pair of 2.4 mm-thick Pyrex glass sheets and irradiated from either side with ultraviolet light using a UV irradiator (light source: a 3 kW metal halide lamp, irradiation distance 125 mm, conveyer speed 1 m/min., wavelength 250–450 nm) for 2 minutes each side or a total of 4 minutes.

Degree of gelation: 94%

EXAMPLES 33–36

In the preparation of a cinnamic acid-polysaccharide derivative of formula (14) and the corresponding crosslinked cinnamic acid-polysaccharide derivative, chitosan was used for $P^2$ and an amide linkage was used for the B-$P^2$ bond. 33-1: Preparation of a photocurable film [compound (2-1-CHS)] incorporated with compound (2-1)

In 1 ml of dimethylformamide (DMF) was dissolved 44 mg (0.2 mmol) of compound (2-1), and under ice-cooling, 400 µl of 0.5 M dimethylphosphinothioyl chloride/DMF solution and 28 µl (0.2 mmol) of triethylamine were added. The mixture was stirred at room temperature for 10 minutes and then added to a solution of 290 mg (2.0 mmol/GlcN) of chitosan (Seikagaku Corporation) in 50 ml 2% acetic acid/50 ml methanol. This mixture was stirred at room temperature for 24 hours, after which it was diluted with 1 ml of 1M aqueous sodium hydroxide solution and poured into 250 ml of ethanol, followed by centrifugation (2500 rpm×5 min.). The sediment was washed three times with 80% ethanol and dissolved in 150 ml of water and the solution was cast in a 96 mm×137 mm square-well dish and dried in an oven at 45° C. to provide a transparent film weighing 320 mg. 33-2: Preparation of a cured film by UV crosslinking of the photocurable film [compound/(2-1-CHS)]

The film prepared in Example 33-1 was sandwiched between a pair of 2.4 mm-thick Pyrex glass sheets and irradiated from either side with ultraviolet light using a UV irradiator (light source: a 3 kW metal halide lamp, irradiation distance 125 mm, conveyer speed 1 m/min., wavelength 250–450 nm) for 4 minutes each side or a total of 8 minutes to provide a water-insoluble film.

EXAMPLES 34–36

Using the cinnamic acid derivatives listed in Table 1, photocurable films and cured films were prepared in accordance with the procedure of Example 33.

EXAMPLES 37–42

The cinnamic acid-polysaccharide derivatives of formula (15) and the corresponding crosslinked cinnamic acid-polysaccharide derivatives, in which $P^1$ represents hyaluronic acid.

EXAMPLE 37

37-1: Preparation of a photocurable film [compound (3a-1-HA)] incorporated with compound (3a-1)

In 50 ml of water was dissolved 200 mg (0.5 mmol disaccharide unit) of a hyaluronic acid with an average molecular weight of 800,000, followed by addition of 10 ml of 1,4-dioxane. Under ice-cooling, 200 µl of 0.5 M N-hydroxysuccinimide/dioxane solution and 200 µl of 0.25 M aqueous solution of a water-soluble carbodiimide were successively added and, after 2 minutes of stirring, 1 ml of an aqueous solution of 12 mg (0.05 mmol) of compound (3a-1) was added. The mixture was stirred at room temperature for 3 hours and 40 minutes, and then 350 ml of a saturated sodium acetate/ethanol solution was added 80 as to precipitate the objective compound. The precipitate was separated by centrifugation (2500 rpm×5 min.). The sediment was washed three times with a mixture of water-ethanol and dissolved in 40 ml of water. The solution was cast in a square-well dish (90 mm×62 mm) and dried in an oven at 45° C. to provide a film. Yield 182 mg. The film had a DS of 1.7% as determined by its absorbance. 37-2: Preparation of a cured film by UV crosslinking of the photocurable film [compound (3a-1-HA)]

The film prepared in Example 37-1 was sandwiched between a pair of 2.4 mm-thick Pyrex glass sheets and irradiated from either side with ultraviolet light using a UV irradiator (light source: a 3 kW metal halide lamp, irradiation distance 125 mm, conveyer speed 1 m/min., wavelength 250–450 nm) for 2 minutes each side or a total of 4 minutes.

Degree of gelation: 99%

EXAMPLES 38–42

Using the cinnamic acid derivatives listed in Table 1, photocurable films and cured films were prepared in accordance with the procedure of Example 37.

EXAMPLES 43

In the preparation of a cinnamic acid-polysaccharide derivative of formula (13) and the corresponding crosslinked cinnamic acid-polysaccharide derivative, chondroitin sulfate was used for $P^1$. The A—$P^1$ linkage is the amide linkage involving the carboxyl group or sulfate group of $P^1$. 43-1: Preparation of a photocurable chondroitin sulfate film compound (1a-4-CS)] incorporated with compound (1a-4) Using sodium chondroitin sulfate in lieu of sodium hyaluronate, the title compound was synthesized following essentially the procedure described in Example 25-1. DS=0.79%. 43-2: Preparation of a cured film by UV crosslinking of the photocurable film [compound (1a-4-CS)]

The film prepared in Example 43-1 was sandwiched between a pair of 2.4 mm-thick Pyrex glass sheets and irradiated from either side with ultraviolet light using a UV irradiator (light source: a 3 kW metal halide lamp, irradiation distance 125 mm, conveyer speed 1 m/min., wavelength 250–450 nm) for 2 minutes each side or a total of 4 minutes.

EXAMPLE 44

In the preparation of a cinnamic acid-polysaccharide derivative of formula (14) and the corresponding crosslinked cinnamic acid-polysaccharide derivative, chondroitin sulfate was used for $P^{2.}$ The B-$P^2$ linkage is an ester linkage involving the hydroxyl group of $P^2$.

44-1: Preparation of a photocurable chondroitin sulfate film [compound (2-1-CS)] incorporated with compound (2-1)

In this example, compound (2-1) was introduced into the hydroxyl group of chondroitin sulfate (mol. wt. 30,000) by an ester linkage.

In 0.5 ml of dimethylformanide (DMF) was dissolved 13 mg (0.06 mmol) of compound (2-1), and under ice-cooling, 120 µl of 0.5 M dimethylphosphinothioyl chloride solution and 10 µl (0.06 mmol) of triethylamine were added. After the mixture was stirred at room temperature for 10 minutes, a previously prepared solution of 150 mg (0.3 mmol) of chondroitin sulfate tributylamine salt in 17 ml DMF was added, followed by addition of 7 mg (0.06 mmol) of 4-dimethylaminopyridine. The mixture was stirred at room temperature for 24 hours. To this reaction mixture was added 2 ml of 5% aqueous sodium hydrogen carbonate solution and the mixture was poured into 150 ml of saturated sodium acetate-ethanol, followed by centrifugation (2500 rpm×5 min.). The sediment was washed three times with 80% ethanol and dissolved in 70 ml of water and the solution was cast in a 35 mm×65 mm square-well dish, and dried in an oven at 45° C. to provide a transparent film weighing 174 mg (DS=18%). 44-2: Preparation of a cured film by UV crosslinking of the photocurable film (compound (2-1-CS)]

The film prepared in Example 44-1 was sandwiched between a pair of 2.4 mm-thick Pyrex glass sheets and irradiated from either side with ultraviolet light using a UV irradiator (light source: a 3 kW metal halide lamp, irradiation distance 125 mm, conveyer speed 1 m/min., wavelength 250–450 nm) for 4 minutes each side or a total of 8 minutes. Degree of gelation 21%.

EXAMPLES 45–50

In the preparation of a cinnamic acid-polysaccharide derivative of formula (15) and the corresponding crosslinked cinnamic acid-polysaccharide derivative, chondroitin sulfate was used for $P^1$. The $C-P^1$ linkage is the amide linkage with the carboxyl group or sulfate group of $P^1$.

EXAMPLE 45

45-1: Preparation of a photocurable chondroitin sulfate film [compound (3a-1-CS)] incorporated with compound (3a-1)

Using sodium chondroitin sulfate in lieu of sodium hyaluronate, the title compound was synthesized essentially following the procedure described in Example 37-1. (DS= 6%)

45-2: Preparation of a cured film by UV crosslinking of the photocurable film [compound (3a-1-CS)]

The film prepared in Example 37-1 was sandwiched between a pair of 2.4 mm-thick Pyrex glass sheets and irradiated from either side with ultraviolet light using a UV irradiator (light source: a 3 kW metal halide lamp, irradiation distance 125 mm, conveyer speed 1 m/min., wavelength 250–450 ram) for 2 minutes each side or a total of 4 minutes.

Degree of gelation: 73%

EXAMPLES 46–50

Using the cinnamic acid derivatives listed in Table 1, photocurable films and cured films were prepared in accordance with the procedure of Example 45.

The results obtained in the foregoing Examples 22–50 are summarized in Tables 1 and 2.

TABLE 1

| | Cinnamic Acid-Polysaccharide Derivative | Cinnamic Acid Derivative | DS (%) | UV Irradiation Time (min.) | Degree of Gelation (%) |
|---|---|---|---|---|---|
| Example 22 | 1a-1-HA | 1a-1 | 0.58 | 8 | 107 |
| Example 23 | 1a-2-HA | 1a-2 | 0.45 | 8 | 82 |
| Example 24 | 1a-3-HA | 1a-3 | 0.46 | 8 | 95 |

TABLE 1-continued

| | Cinnamic Acid-Polysaccharide Derivative | Cinnamic Acid Derivative | DS (%) | UV Irradiation Time (min.) | Degree of Gelation (%) |
|---|---|---|---|---|---|
| Example 25 | 1a-4-HA | 1a-4 | 0.37 | 8 | 92 |
| Example 26 | 1a-5-HA | 1a-5 | 0.36 | 8 | 97 |
| Example 27 | 1a-6-HA | 1a-6 | 0.25 | 8 | 91 |
| Example 28 | 1a-7-HA | 1a-7 | 0.39 | 8 | 99 |
| Example 29 | 1a-8-HA | 1a-8 | 0.7 | 4 | 94 |
| Example 30 | 1a-9-HA | 1a-9 | 0.99 | 8 | — |
| Example 31 | 1a-10-HA | 1a-10 | 1.0 | 8 | — |
| Example 32 | 1a-11-HA | 1a-11 | 0.7 | 8 | — |
| Example 33 | 2-1-CHS | 2-1 | — | 8 | — |
| Example 34 | 2-2-CHS | 2-2 | — | 8 | — |
| Example 35 | 2-3-CHS | 2-3 | — | 8 | — |
| Example 36 | 2-4-CHS | 2-4 | — | 8 | — |

TABLE 2

| | Cinnamic Acid-Polysaccharide Derivative | Cinnamic Acid Derivative | DS (%) | UV Irradiation Time (min.) | Degree of Gelation (%) |
|---|---|---|---|---|---|
| Example 37 | 3a-1-HA | 3a-1 | 1.0 | 4 | 95 |
| Example 38 | 3a-2-HA | 3a-2 | 0.4 | 4 | 92 |
| Example 39 | 3a-3-HA | 3a-3 | 0.3 | 4 | 94 |
| Example 40 | 3a-4-HA | 3a-4 | 1.7 | 4 | 99 |
| Example 41 | 3a-5-HA | 3a-5 | 1.8 | 4 | 97 |
| Example 42 | 3a-6-HA | 3a-6 | 1.3 | 4 | 99 |
| Example 43 | 1a-4-CS | 1a-4 | 0.79 | 4 | — |
| Example 44 | 2-1-CS | 2-1 | 18 | 8 | 21 |
| Example 45 | 3a-1-CS | 3a-1 | 6 | 4 | 73 |
| Example 46 | 3a-2-CS | 3a-2 | 7 | 4 | 48 |
| Example 47 | 3a-3-CS | 3a-3 | 6 | 4 | 67 |
| Example 48 | 3a-4-CS | 3a-4 | 7 | 4 | 76 |
| Example 49 | 3a-5-CS | 3a-5 | 8 | 4 | 65 |
| Example 50 | 3a-6-CS | 3a-6 | 7 | 4 | 75 |

Crosslinking group-dependent characteristics of photocured hyaluronic acid films In the following example, differences in film characteristics due to differences in the value of n in the structural formula of the hyaluronic acid derivative incorporated with a cinnamic acid derivative of the structural formula $H_2N—(CH_2)_n—OCOCH=CH—Ph$ (1-A) (Ph represents phenyl) were mainly investigated.

EXAMPLE 51

Figure 2:
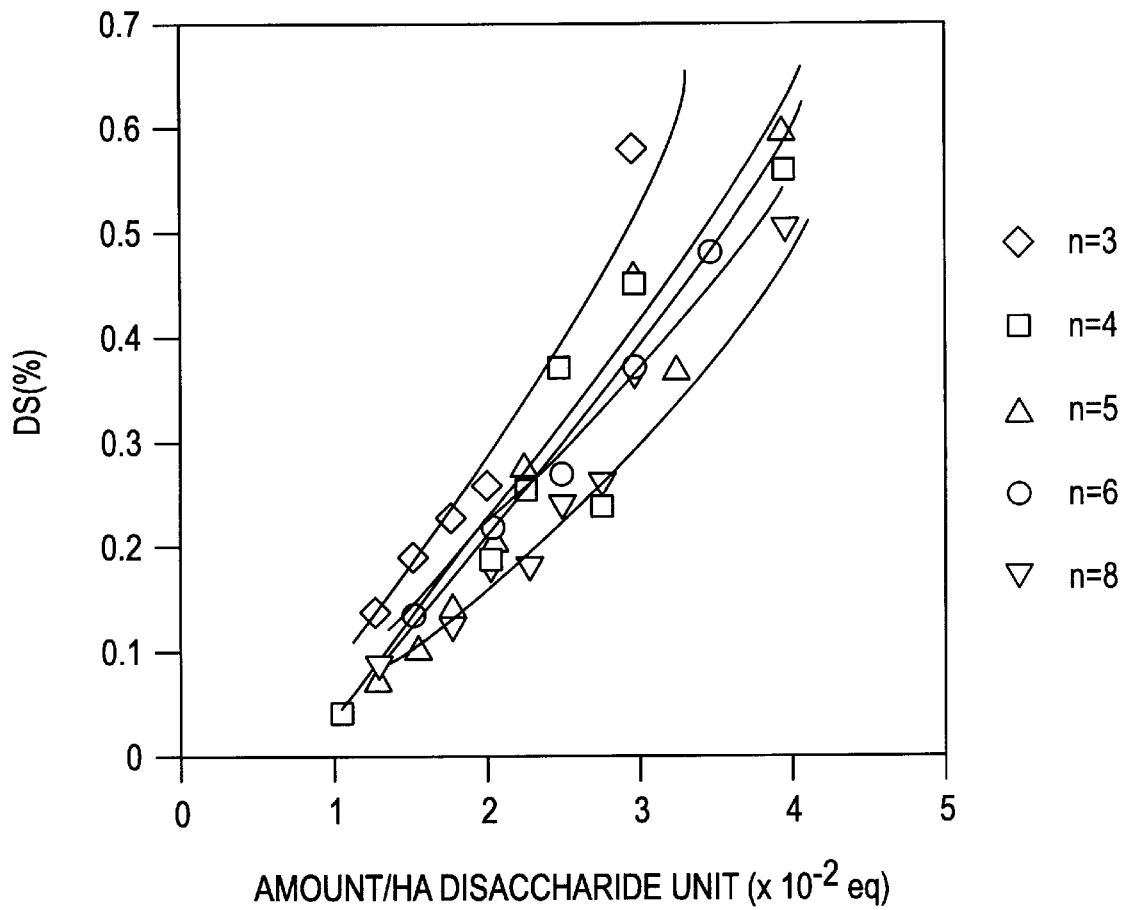
FIG. 2 graphically shows the result obtained in Example 51, indicating the reactivity dependent on the spacer carbon number.

In this example, differences in the reactivity to hyaluronic acid in the introduction of the cinnamic acid derivative according to differences in the value of n in the above compound (1-A) under otherwise the identical conditions were investigated (FIG. 2). In FIG. 2, the abscissa represents the amount of cinnamic acid derivative used per hyaluronic acid disaccharide unit under the following conditions and the ordinate represents the degree of substitution DS.
[Reaction conditions]
 Host compounds sodium hyaluronate (MM 800,000)
 Solvent: water-dioxane (2:1)
 Condensing agent: N-hydroxysuccinimide, 2 molar equivalents/(1-A)
 Water-soluble carbodiimide, equimolar equivalent/(1-A)
 Reaction temperature: room temperature
 Reaction time: 24 hrs.
 FIG. 2 shows that the longer the methylene chain is, that is to say the larger the value of n is, the lower is the reactivity. Thus, in the reaction in the aqueous solvent, a larger value of n results in an increase, though slight, in the hydrophobicity of compound (1-A) itself and a commensurate decrease in affinity for the solvent or substrate, lowering the reactivity.

EXAMPLE 52

Figure 3:
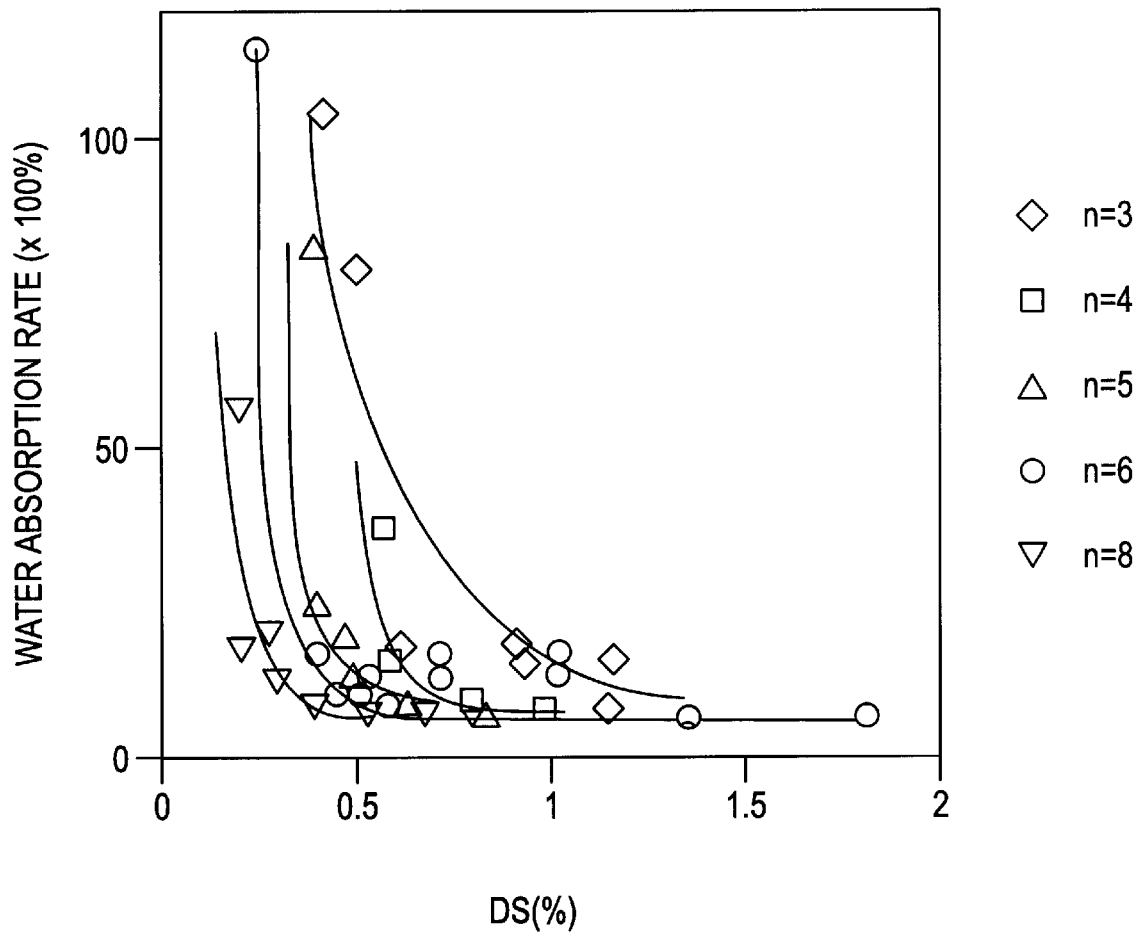
FIG. 3 graphically shows the result obtained in Example 52, indicating the relationship between water absorption rate and DS.

In this example, differences in water absorption rate due to differences in the DS of the crosslinked hyaluronic acid film as exposed to UV light for 4 minutes were investigated introducing a variety of cinnamic acid derivatives varying in the value of n in the formula (1-A) (FIG. 3). The water absorption rate is calculated by the following equation.

Water absorption rate (%)=(wet weight of film–dry weight of film)/dry weight of film×100

Dry weight of film: weight after drying of cured film

Wet weight of film: weight after 1-hour immersing in water (wetting) of cured film As DS is decreased, all cured films show steep increases in water absorption rate at below of a specific level of DS. The reason is as follows. A decrease in DS results in a decrease in crosslinking density, rendering the network structure more coarse and enabling to absorb more water. However, a further decrease in crosslink density detracts from the insolubilizability of the film. Analysis of responses due to differences in n reveals that the larger the value of n is, the greater is the graph shift to downfield on the DS scale. This means that a larger value of n provides a network structure which is able to hold more water and can be insolubilized at a lower value of DS. While construction of a network structure is implemented by photocrosslinking reaction through UV light irradiation, the above results suggest that, when the value of DS being held constant, the photoreactive hyaluronic acid derivative containing a cinnamic acid derivative with a larger value of n is easy to form a network structure, and thus indicate that the photoreactivity of the cinnamic acid derivative has a significant influence on characteristics of the cured film.

EXAMPLE 53

Figure 4:
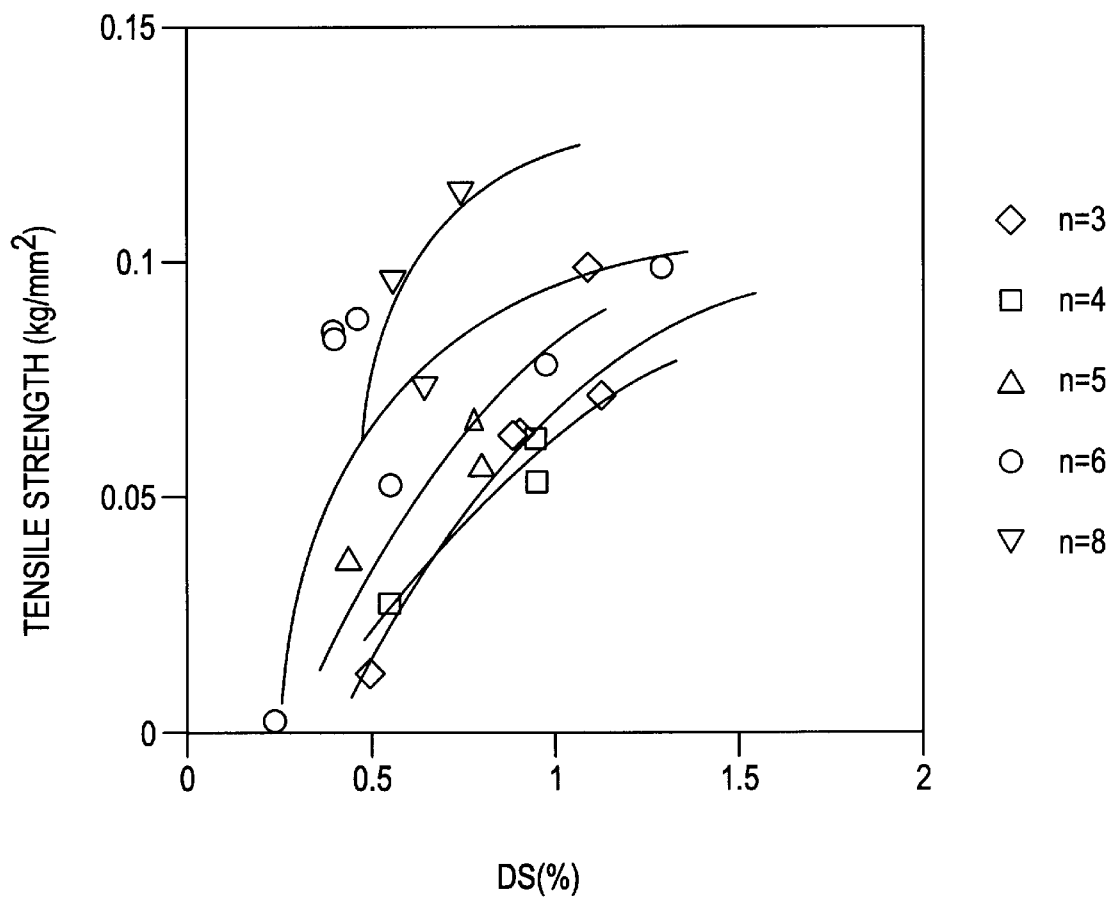
FIG. 4 graphically shows the result obtained in Example 53, indicating the relationship between tensile strength and DS.

In this example, the responses of tensile strength according to differences in DS of the crosslinked hyaluronic acid films prepared by introducing a variety of cinnamic acid derivatives varying in the value of n in the compound (1-A) and exposing films with UV light for 4 minutes were investigated (FIG. 4). The tensile strength was invariably measured for the water-immersed film using a rheometer.

It is apparent from FIG. 4 that the larger the value of DS is, the higher is the crosslinking density and, hence, the higher is the tensile strength. Analysis of responses according to differences in the value of n shows that the larger the value of n is, the greater is the graph shift to downfield on the DS scale, indicating that, when the value of DS being held constant, a larger value of n provides higher tensile strength.

As described in Example 52, for the same DS, a larger value of n results in a higher photoreaction efficiency to provide a film of higher crosslinking density. Since tensile strength is considered to be proportional to crosslinking density, a larger value of n provides a higher tensile strength.

EXAMPLE 54

Figure 5:
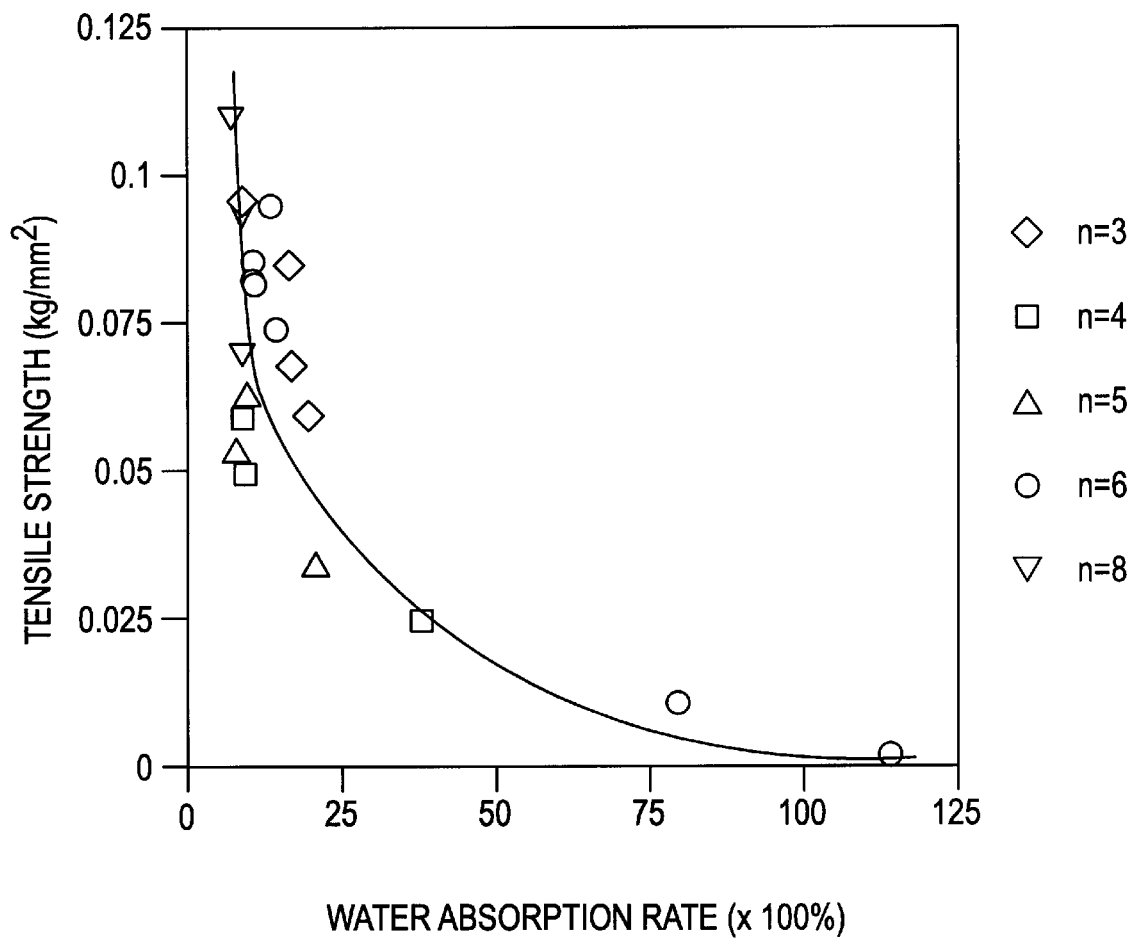
FIG. 5 graphically shows the result obtained in Example 53, indicating the relationship between tensile strength and water absorption rate.
Figure 6:
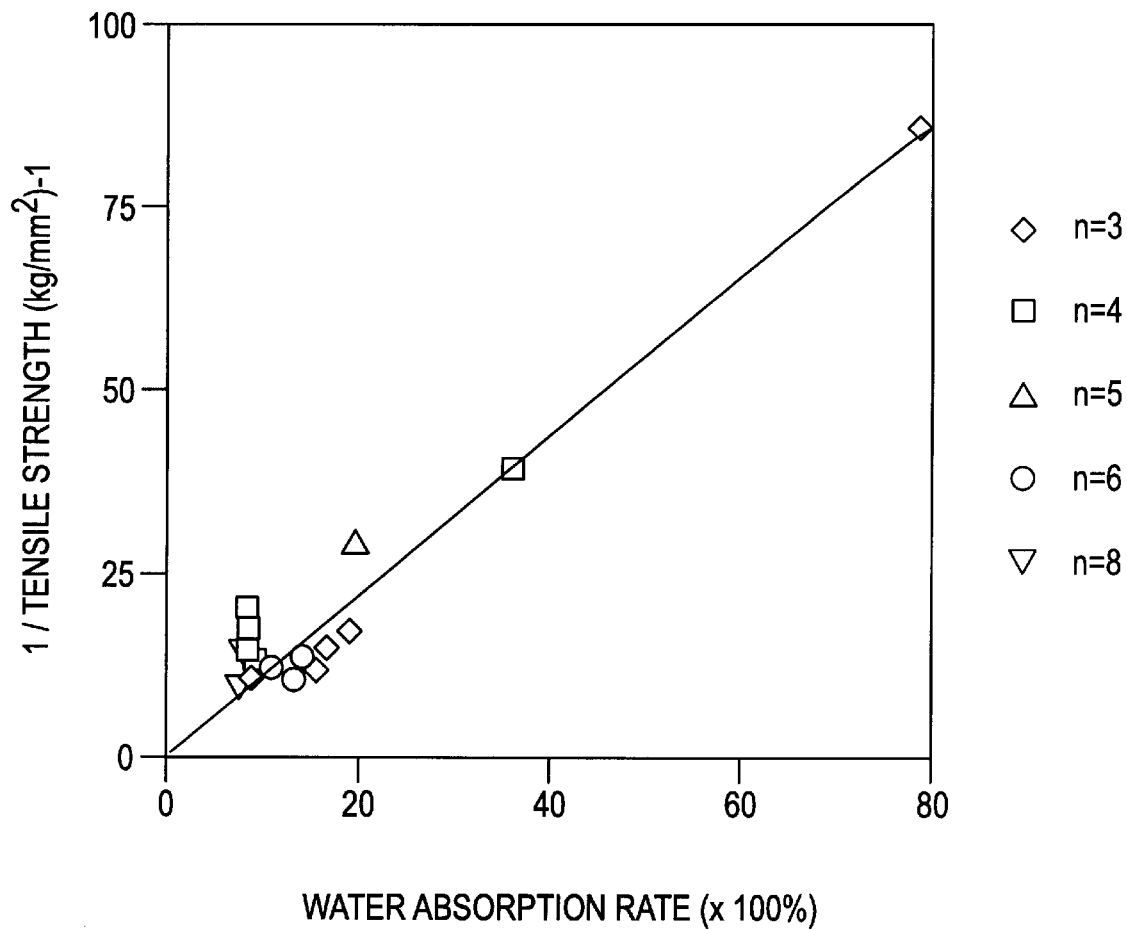
FIG. 6 graphically shows the result obtained in Example 54, indicating the relationship between the reciprocal of tensile strength and water absorption rate.

In this example, the responses of tensile strength due to differences in the water absorption rate of the crosslinked hyaluronic acid films obtained by introducing a variety of cinnamic acid derivatives varying in the value of n in said compound (1-A) and exposing films with UV light for 4 minutes were investigated (FIGS. 5 and 6).

FIG. 5 was constructed by plotting water absorption data on the abscissa and tensile strength data on the ordinate. It is clear that regardless of the value of n, the water absorption rate is inversely proportional to the tensile strength. FIG. 6 was constructed by plotting the reciprocals of tensile strength data on the ordinate, where a linear relation was obtained.

EXAMPLE 55

Figure 7:
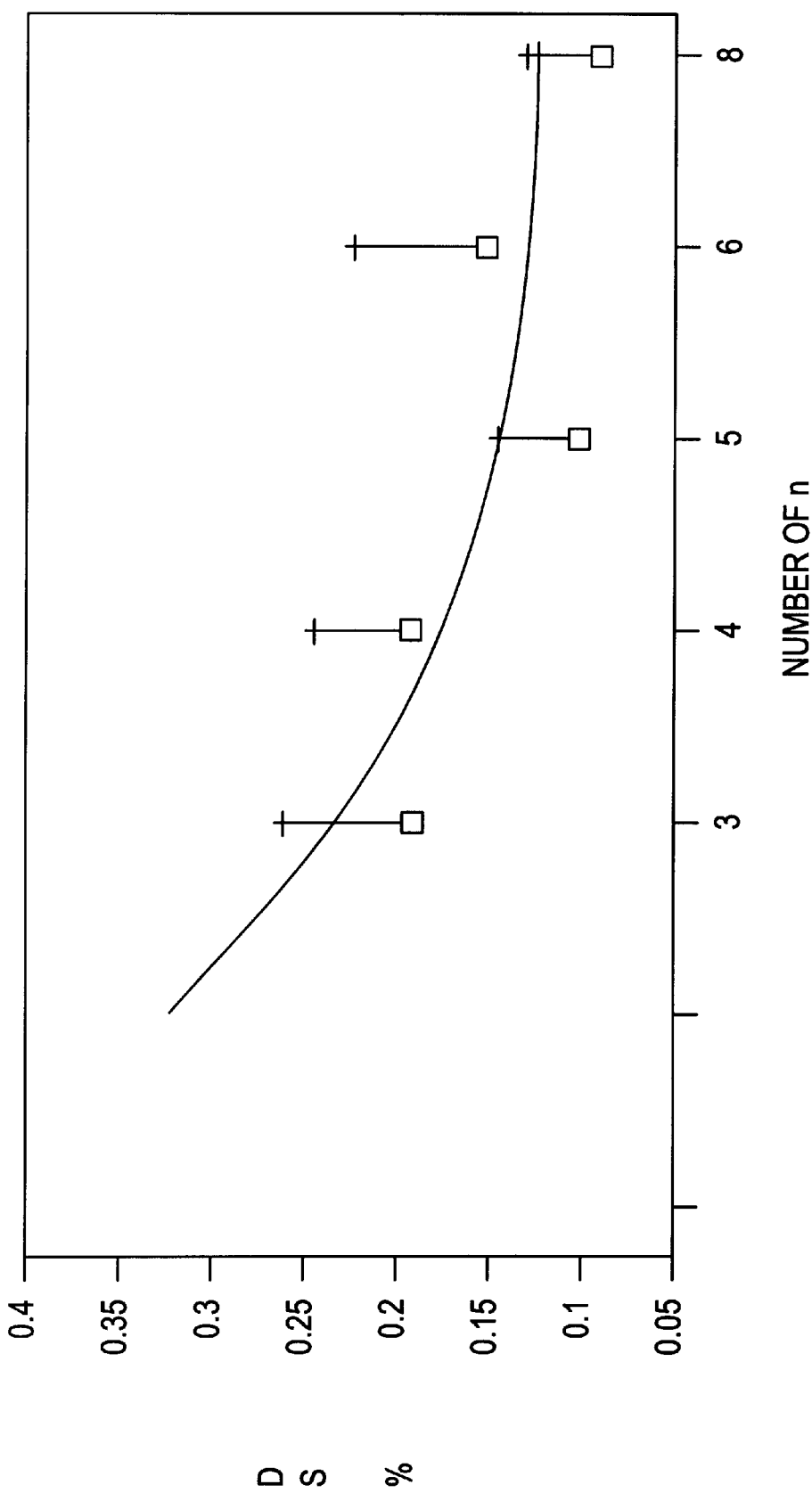
FIG. 7 graphically shows the result obtained in Example 55, indicating the critical point of insolubilization.

In this example, the critical point of insolubilization of the crosslinking hyaluronic acid films obtained by introducing a variety of cinnamic acid derivatives varying in the value of n in the compound (1-A) and exposing films to UV light for 8 minutes was observed (FIG. 7). The abscissa represents n and the ordinate represents DS. Each □ plot on the graph represents DS at which the film is solubilized and each + plot represents DS at which insolubilization of the film begins to occur, with the critical point of insolubilization lying between □ and +. This critical point of insolubilization is also the point of phase transition from film to gel form.

EXAMPLE 56

In this example, the effect of cinnamic acid derivatives other than the compound (1-A), namely the derivatives having structural formula represented by formulas (7) and (9), was investigated.

The relative reactivity of the following crosslinkable compounds to sodium hyaluronate (MW 800,000) was investigated as in Example 51. These cinnamic acid derivatives shown below have an equivalent number of atoms in the backbone chain between the spacer amino group and the cinnamoyl group, but are different in spacer structure, e.g. presence of an ether linkage, an amide linkage or a branch chain in addition to the methylene chain.

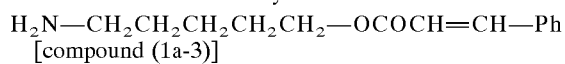
[compound (1a-3)]

[compound (1a-7)]

[compound (1a-9)]

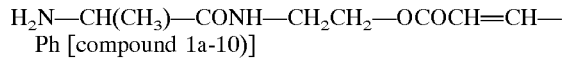
Ph [compound 1a-10)]

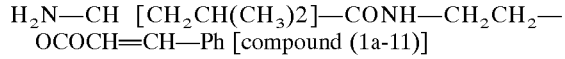
OCOCH=CH—Ph [compound (1a-11)]

Figure 8:
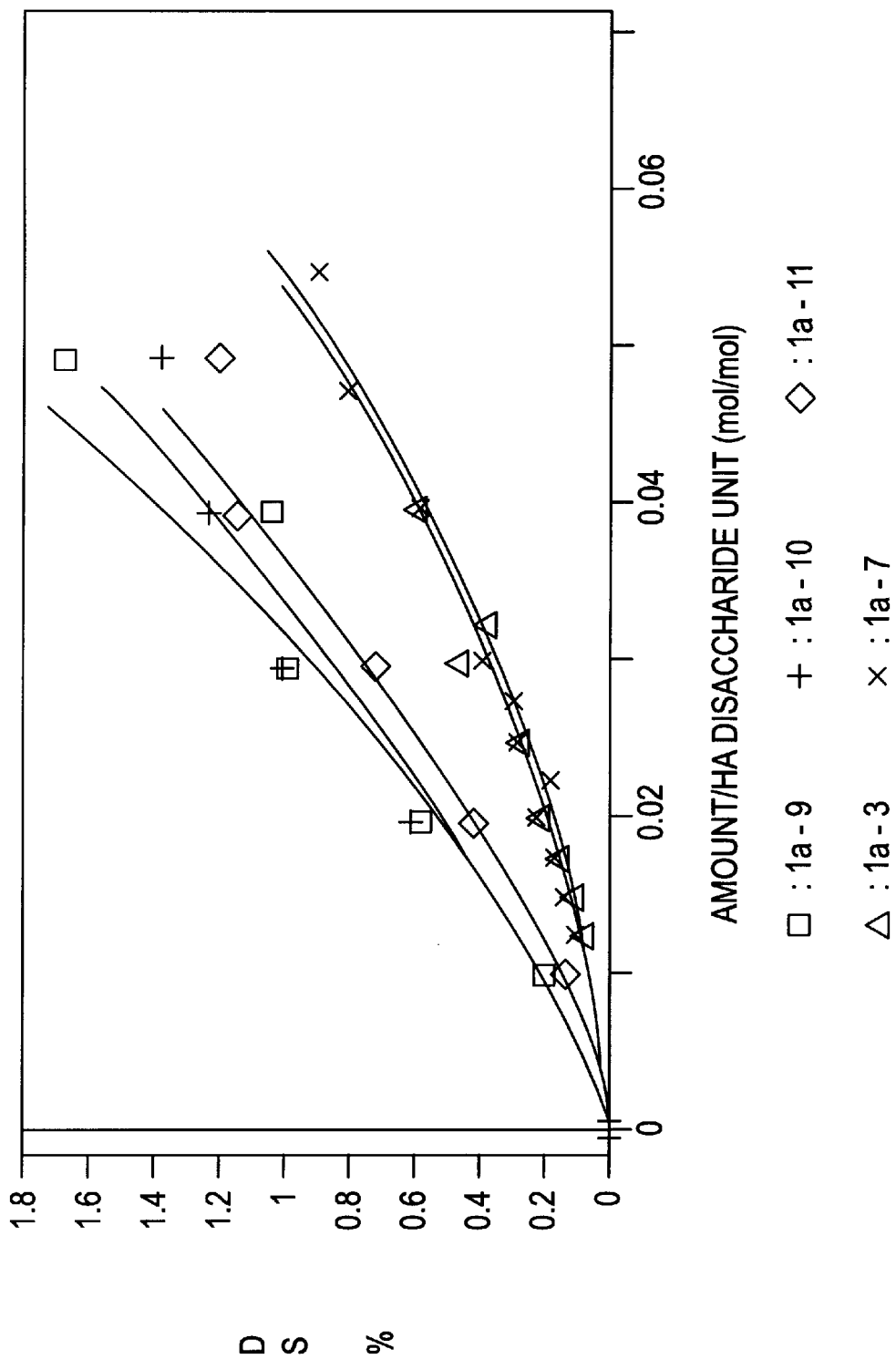
FIG. 8 graphically shows the result obtained in Example 56, indicating the relative reactivity of the moiety of the spacer other than the methylene chain.

The result is shown in FIG. 8, where the abscissa represents the charged amount of each cinnamic acid derivative per hyaluronic acid disaccharide unit and the ordinate represents the degree of substitution (DS).

The compounds having an amide linkage in the spacer are particularly reactive and, among them, less branched compounds (1a-9) and (1a-10) exhibited better reactivity. This is considered to be a reflection of the effect of hydrophilicity of the spacer structure.

EXAMPLE 57

For the five compounds described in Example 56, the relationship between DS and water absorption rate was investigated by the procedure described in Example 52.

Figure 9:
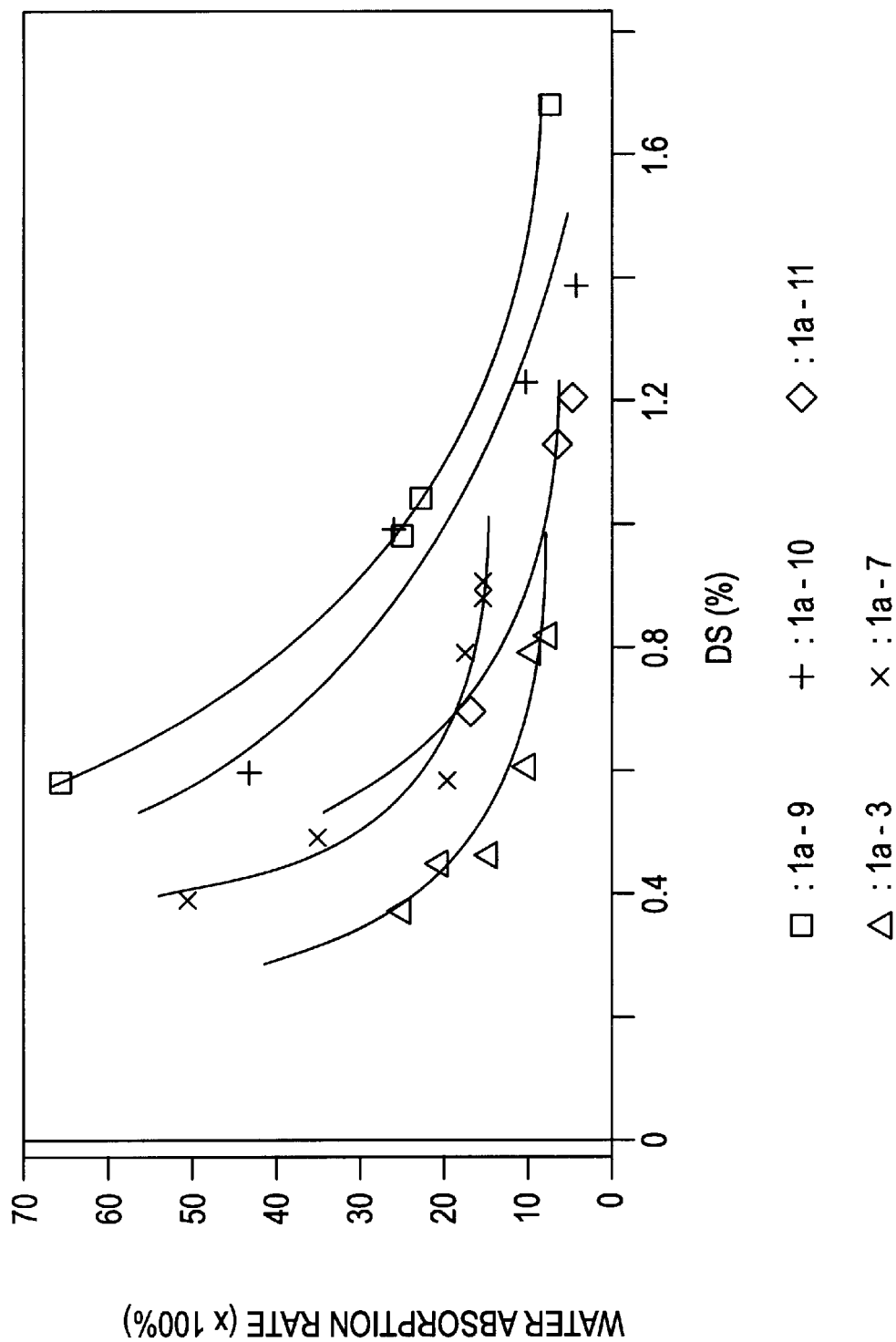
FIG. 9 graphically shows the result obtained in Example 57, indicating the relationships between DS and water absorption rate of various spacer structures other than the methylene chain.

The result is shown in FIG. 9. The hydrophilic compounds having an amide linkage and a lesser degree of branching in spacer structure, (1a-9-HA) and (1a-10-HA), show higher absorption rates at the high DS level as compared with the other compounds. The water absorption rate is markedly influenced by crosslinking density and those compounds with high water absorption rates are lower in crosslinking density than the other compounds. While the crosslinked structure is constructed by photoreaction as described in Example 52, the hyaluronic acid derivative containing the above compound having a highly hydrophilic spacer structure appears to be less reactive for this photoreaction, whereas the derivative with a highly hydrophobic structure shows higher photoreactivity.

While this photoreaction is carried out by casting an aqueous solution of the photoreactive hyaluronic acid derivative into a film and irradiating the film with ultraviolet light, it appears that a cinnamic acid derivative having greater hydrophobicity in film formation tends to aggregate and take orientation, thus providing for a better environment for photoreaction.

The intensity of hydrophobicity of the above compounds is in the order of compound (1a-3)>compound (1a-7) >compound (1a-11)>compound (1a-10)>compound (1a-9).

The photoreactivity in photoreaction increases in the above order of hydrophobicity and the reactivity to the hyaluronic acid of Example 56 conversely increases in the decreasing order of hydrophobicity.

EXAMPLES 58–61
Enzymatic degradability

A photocurable film prepared according to Example 25 was irradiated with UV light under the conditions shown in Table 2 and the area swelling ratio, degree of gelation, and course of enzymatic degradation (decomposition rate) of the cured film were evaluated (Table 3).

The conditions of enzymatic degradation were as follows.

Buffer: 0.2 M acetic acid-sodium hydroxide (pH 6)
Enzyme: Hyaluronidase (sheep testis origin), 100 U/mg.
Temperatures 37° C.
Assay method: The amount of low molecular weight hyaluronic acid released from the cured film by enzymatic degradation was measured by the carbazole method and the decomposition rate was calculated by comparison with the initial weight.

Decomposition rate (%)=(weight of hyaluronic acid released into buffer/initial weight of cured film)×100 tive and the film of cured hyaluronic acid derivative are hereinafter referred to as a photocurable film and a cured film, respectively.

EXAMPLE 62

(1) Preparation of a photocurable film (compound 62) using compound (3a-4)

In 50 ml of water was dissolved 200 mg (0.5 mmol/monomer) of sodium hyaluronate with an average molecular weight of 1,000,000, followed by addition of 10 ml of 1,4-dioxane. Under ice-cooling, 200 µl of 0.5 M solution of N-hydroxysuccinimide/dioxane and 200 µl of 0.25 M aqueous solution of 1-ethyl-3-(3-dimethylaminopropyl) carbodiimide hydrochloride (EDC) were successively added and, after 2 minutes of stirring, 1 ml of an aqueous solution of 12 mg (0.05 mmol) of compound (3a-4) was added. After the mixture was stirred at room temperature for 3 hours and 40 minutes, 350 ml of a saturated sodium acetate/ethanol solution was added so as to precipitate the objective compound. The precipitate was separated by centrifugation (2500 rpm×5 min.). The sediment was washed three times with a mixed solution of water and ethanol and dissolved in 40 ml of water. The solution was cast in a square-well dish (each, 90 mm×62 mm) and dried in an oven at 45° C. to provide samples of a film. Thus, a photocurable film of compound 62 having a DS of 1.7% as determined by its absorbance was obtained in a yield of 182 mg.

(2) Preparation of a cured film by UV crosslinking of the photocurable film of compound 62

The film prepared in (1) was sandwiched between a pair of 2.4 mm-thick Pyrex glass (trade name) sheets, fixed on a conveyer and irradiated from either side with ultraviolet light using a UV irradiator [Ushio Denki K. K., Type UVC-2531, light source: a 3 kW metal halide lamp (length: 1 m), irradiation distance 125 mm, conveyer speed 1 m/min] for 4 minutes each side to obtain a cured film. Degree of gelation: 99%

EXAMPLE 63

A photocurable film and a cured film were prepared in accordance with the procedure of Example 62 except for replacing a photodimerizable-croselinkable compound of Example 62 with compound (3a-5).

EXAMPLE 64

(1) Preparation of a photocurable film (compound 64) using compound (3a-6)

TABLE 3

| Example | DS | UV Irradiation (min.) | Area Swelling Ratio (× 100%) | Degree of Gelation (%) | Time Course of Enzymatic Degradation (decomposition rate, %) | | | | | |
|---|---|---|---|---|---|---|---|---|---|---|
| | | | | | 0.5 H | 3 H | 6 H | 1 D | 2 D | 3 D |
| 58 | 1.5 | 4  | 2.23 | 96  | 17 | 70 | 88 | 96 | 93 | 92 |
| 59 | 1.5 | 8  | 1.96 | 99  | 10 | 63 | 87 | 93 | 93 | 89 |
| 60 | 1.5 | 12 | 1.99 | 100 | 10 | 50 | 66 | 76 | 75 | 80 |
| 61 | 0.6 | 8  | 3.24 | 93  | 46 | 89 | 89 | 89 | 89 | 93 |

H: hour; D: day.

EXAMPLES 62–79
Preparation of film of photocurable hyaluronic acid derivative and film of cured hyaluronic acid derivative A film of photocurable hyaluronic acid derivative and a film of cured hyaluronic acid derivative of the present invention were respectively prepared in the following examples. The film of photocurable hyaluronic acid deriva- In 50 ml of water was dissolved 320 mg (0.8 mmol/monomer) of sodium hyaluronic with an average molecular weight of 1,000,000, followed by addition of 25 ml of 1,4-dioxane. Under ice-cooling, 320 µl of 0.5 M N-hydroxy-succinimide/dioxane solution and 320 µl of 0.25 M EDC aqueous solution were successively added. The mixture was stirred for 10 minutes and 1 ml of an aqueous solution of 30 mg (0.08 mmol) of compound (3a-6) was added. After the mixture was stirred at room temperature for 2 hours, 250 ml of a saturated sodium acetate/ethanol solution was added so as to precipitate the objective compound. The precipitate was separated by centrifugation (2500 rpm×5 min.). The sediment was washed three times with water-ethanol and dissolved in 300 ml of water. After the liquid volume was decreased to about 50 ml by concentration under reduced pressure, the solution was cast in a square-well dish (90 mm×62 mm) and dried in an oven at 45° C. to provide a film. A photocurable film having a DS of 0.9% as determined by UV was obtained in a yield of 258 mg. (2) Preparation of a cured film by UV crosslinking of the photocurable film of compound 64

The film prepared in (1) was sandwiched between a pair of 2.4 mm-thick Pyrex glass sheets and irradiated with ultraviolet light in the same manner as in Example 62 (2) to prepare a cured film. Degree of gelation: 113%

EXAMPLE 65

A photocurable film and a cured film were prepared using compound (3a-6) in accordance with the procedure of Example 64.

EXAMPLE 66

(1) Preparation of a photocurable film (compound 66) using compound (3a-1)

Using 320 mg (0.8 mmol/monomer) of sodium hyaluronate having an average molecular weight of 1,000,000 and 1 ml of a solution of 24 mg (0.08 mmol) of compound (3a-1), a film was prepared in the same manner as in Example 64 (1). Thus, a photocurable film having a DS of 2.5% as determined by NMR in a yield of 272 mg.
(2) Preparation of a cured film by UV crosslinking of the photocurable film of compound 66

The film prepared in (1) was sandwiched between a pair of 2.4 mm-thick Pyrex glass sheets and irradiated with ultraviolet light in the same manner as in Example 62 (2) to provide a cured film. Degree of gelation; 108%

EXAMPLE 67

A photocurable film and a cured film were prepared using compound (3a-1) in accordance with the procedure of Example 66.

EXAMPLE 68

A photocurable film and a cured film were prepared in accordance with the procedure of Example 67 except for replacing a photodimerizable curable compound of Example 67 with compound (3a-2).

EXAMPLE 69

(1) Preparation of a photocurable film (compound 69) using compound (3a-3)

In 80 ml of water was dissolved 320 mg (0.8 mmol/monomer) of sodium hyaluronate with an average molecular weight of 1,000,000, followed by addition of 40 ml of 1,4-dioxane. Under ice-cooling, 160 µl of 0.5 M N-hydroxysuccinimide/dioxane solution and 160 µl of 0.25 M aqueous solution of EDC were successively added and, after 2 minutes of stirring, 1 ml of an aqueous solution of 17 mg (0.04 mmol) of compound (3a-3) was added. The mixture was stirred at room temperature for 5 hours, and then 250 ml of a saturated sodium acetate/ethanol solution was added so as to precipitate the objective compound. The precipitate was separated by centrifugation (2500 rpm×5 min.). The sediment was washed three times with a mixture of water-ethanol and dissolved in 75 ml of water. The solution was cast in a square-well dish (90 mm×62 mm) and dried in an oven at 45° C. to provide a film. Thus, a photocurable film having a DS of 0.6% as determined by its absorbance was obtained in a yield of 370 mg.
(2) Preparation of a cured film by UV crosslinking of the photocurable film of compound 69

The film prepared in (1) was sandwiched between a pair of 2.4 mm-thick Pyrex glass sheets and irradiated with ultraviolet light in the same manner as in Example 62 (2) to obtain a cured film. Degree of gelation: 87%

EXAMPLE 70

A photocurable film and a cured film were prepared using compound (3a-3) in accordance with the procedure of Example 69.

EXAMPLE 71

71-1: Synthesis of Boc-NH(CH$_2$)$_2$O-Cin [compound (1a-13)]

Three ml of chloroform was added to 464 µl (3 mmol) of t-butoxycarbonyl-2-aminoethanol and, under ice-cooling, 417 µl (3 mmol) of triethylamine, 431 µl (3 mmol) of cinnamoyl chloride and 1.83 mg (1.5 mmol) of 4-dimethylaminopyridine were successively added. The mixture was stirred at room temperature for 20 minutes. Ethyl acetate was added to the reaction mixture and washed successively with a 5% aqueous citric acid solution twice, water, a 5% aqueous sodium hydrogen carbonate solution twice, water, and a saturated aqueous sodium chloride solution in a separatory funnel. The solution was dried over anhydrous sodium sulfate which was then filtered off and the filtrate was dried under reduced pressure. The white solid thus precipitated was washed with hexane and dried in vacuo to provide 527 mg (yield 60%) of compound (1a-13).
$^1$H-NNR (CDCl$_3$):

δ (ppm)=1.45 9H s (Boc-), 3.55 2H m (—NHCH$_2$O—), 4.25 2H m (—NHCH$_2$CH$_2$O—), 4.85 1H br (CO NH—), 6.45 1H d (—CH=CHCO—), 7.45 4H dd (Aromatic H), 7.75 1H d (—CH=CHCO—)

71-2: Synthesis of ethyl 2-aminocinnamate hydrochloride [compound (1a-14): HCl.H$_2$N(CH$_2$)$_2$O-Cin]

To 291 mg (1 mmol) of compound (1a-14) was added 2 ml of 4N-HCl/dioxane solution under ice-cooling, and the mixture was stirred at room temperature for 35 minutes. Ether was added to the reaction mixture and the crystals thus precipitated was collected by filtration and washed with ether. The resulting solid was dried in vacuo to provide 173 mg (yield 76%) of compound (1a-14) as white crystals.
(1) Preparation of a photocurable film (compound 71) using compound (1a-14)

In 50 ml of water was dissolved 200 mg (0.5 mmol/monomer) of sodium hyaluronate with an average molecular weight of 1,000,000, followed by addition of 10 ml of 1,4-dioxane. Under ice-cooling, 200 µl of 0.5 M N-hydroxysuccinimide/dioxane solution and 200 µl of 0.25 M aqueous solution of EDC were successively added and, after 5 minutes of stirring, 1 ml of an aqueous solution of 11 mg (0.05 mmol) of compound (1a-14) was added. The mixture was stirred at room temperature for 7 hours, and then 350 ml of a saturated sodium acetate/ethanol solution was added so as to precipitate the objective compound. The precipitate was separated by centrifugation (2500 rpm×5 min.). The sediment was washed three times with a mixture of water-ethanol and dissolved in 80 ml of water. The solution was cast in a square-well dish (90 mm×62 mm) and dried in an oven at 45° C. to provide a film. Thus, a photocurable film having a DS of 0.98% as determined by its absorbance was obtained in a yield of 192 mg.
(2) Preparation of a cured film by UV crosslinking of the photocurable film of compound 71

The film prepared in (1) was sandwiched between a pair of 2.4 mm-thick Pyrex glass sheets and irradiated with ultraviolet light in the same manner as in Example 62 (2) to obtain a cured film. Degree of gelation: 91%

EXAMPLES 72–74

Photocurable films and cured films were prepared in accordance with the procedure of Example 62 except for replacing a photodimerizable curable compound of Example 71 with compounds (1a-1), (1a-2) and (1a-3).

EXAMPLE 75

(1) Preparation of a photocurable film. (compound 75) using, compound (1a-4)

In 50 m of water was dissolved 200 mg (0.5 mmol/monomer) of sodium hyaluronate with average molecular weight of 1,000,000, followed by addition of 10 ml of 1,4-dioxane. Under ice-cooling, 200 $\mu$l of 0.5 M N-hydroxysuccinimide/dioxane solution and 200 $\mu$l of 0.25 M aqueous solution of EDC were successively added and, after 5 minutes of stirring, 1 ml of an aqueous solution of 14 mg (0.05 mmol) of compound (1a-4) was added. The mixture was stirred at room temperature for 7 hours, and then 350 ml of a saturated sodium acetate/ethanol solution was added so as to precipitate the objective compound. The precipitate was separated by centrifugation (2500 rpm×5 min.). The sediment was washed three times with a mixture of water-ethanol and dissolved in 80 ml of water. The solution was cast in a square-well dish (90 mm×62 mm) and dried in an oven at 45° C. to provide a film. Thus, a photocurable film having a DS of 0.57% as determined by its absorbance was obtained in a yield of 196 mg.
(2) Preparation of a cured film by UV crosslinking of the photocurable film of compound 75

The film prepared in (1) was sandwiched between a pair of 2.4 mm-thick Pyrex glass sheets and irradiated with ultraviolet light in the same manner as in Example 62 (2) to obtain a cured film. Degree of gelation: 92%

Cured films were prepared in accordance with the procedures of (1) and (2) except for replacing the above sodium hyaluronate with sodium hyaluronate having a molecular weight of 100,000, 300,000, 500 000 and 800,000.

EXAMPLE 76

A photocurable film and a cured film were prepared in accordance with the procedure of Example 75 except for replacing a photodimerizable curable compound of Example 75 with compound (1a-5).

EXAMPLE 77

(1) Preparation of a photocurable film (compound 77) using compound .(1a-6)

Using 200 mg (0.5 mmol/monomer) of sodium hyaluronate having an average molecular weight of 1,000,000 and 1 ml of a solution of 18 mg.(0.05 mmol) of compound (1a-6), a film was prepared in the same manner as in Example 71 (1). Thus, a photocurable film having a DS of 0.58% as determined by its absorbance in a yield of 194 mg.
(2) Preparation of a cured film by UV crosslinking of the photocurable film of compound 77

The film prepared in (1) was sandwiched between a pair of 2.4 mm-thick Pyrex glass sheets and irradiated with ultraviolet light in the same manner as in Example 62 (2) to obtain a cured film. Degree of gelation: 96%

EXAMPLE 78

A photocurable film and a cured film were prepared in accordance with the procedure of Example 77 except for replacing a photodimerizable curable compound of Example 77 compound (1a-8).

EXAMPLE 79

(1) Preparation of a photocurable film (compound 79) using cinnamic anhydride

In 250 ml of ,water was dissolved 400 mg (1.0 mmol/monomer) of sodium hyaluronate with an average molecular weight of 1,000,000, followed by addition of 125 ml of 1,4-dioxane. Under ice-cooling, 15 ml of a dioxane solution of 139 mg (0.5 mmol) of cinnamic anhydride, 70 $\mu$l (0.5 mmol) of triethylamine and 61 mg (0.5 mmol) of 4-dimethylaminopyridine was added dropwise over 40 minutes. The mixture was stirred at room temperature for 1 hour and the resulting solution was poured into 1.0 l of a saturated sodium acetate/ethanol solution. The precipitate thus obtained was separated by centrifugation, purified by washing three times with water-ethanol and dried under reduced pressure to obtain 380 mg of cinnamoyl hyaluronate as white powder. DS determined by NMR was 2.0%. Endotoxin content was 46.8 pg/mg (dry basis) as determined by colorimetry using diazo-coupling method. After dissolving 380 mg of a photocurable powder in 200 ml of water homogeneously, the solution was concentrated under reduced pressure until the liquid volume was decreased to about 50 ml The solution was poured into a square-well dish (65-mm×90 mm) and dried in a dryer at 40° C. for 2 days to provided a film, Thus, a photocurable film was obtained.
(2) Preparation of a cured film by UV crosslinking of the photocurable film of compound 79

The film prepared in (1) was sandwiched between a pair of 2.4 mm-thick Pyrex glass sheets and irradiated with ultraviolet light in the same manner as in Example 62 (2) to obtain a cured film. Degree of gelation: 85%

Table 4 shows DS and ultraviolet irradiation time (min) of the photocurable film prepared in Examples 62–79 and degree of gelation an wet tensile strength of the corresponding cured films.

Degree of gelation (t)=(redry weight of film/dry weight of film)× 100

Redry weight of film=weight of film which has been immersed in 10,000 times its weight of water for 24 hours, collected by filtration and dried under reduced pressure Dry weight of film weight of film which has been dried under reduced pressure prior to immersion Wet tensile strength is a maximum tensile strength of film, which has been immersed in water for 1 hour, as measured by until it is cut.

TABLE 4

| Example No | Photocurable Film | | | Cured Film | |
|---|---|---|---|---|---|
| | Cinnamic Acid Derivative | DS (%) | UV Irradiation of Bothe side (min) | Degree of Gelation (%) | Wet Tensile Strength (g/mm$^2$) |
| 62 | (3a-4) | 1.7 | 2 × 2 | 99 | 152 |
| 63 | (3a-5) | 1.8 | " | 97 | 77 |
| 64 | (3a-6) | 0.9 | " | 113 | 21 |
| 65 | (3a-6) | 1.3 | " | 99 | 54 |
| 66 | (3a-1) | 2.5 | " | 108 | 38 |
| 67 | (3a-1) | 1.0 | " | 95 | 79 |
| 68 | (3a-2) | 0.4 | " | 92 | 73 |

TABLE 4-continued

| | Photocurable Film | | | Cured Film | |
|---|---|---|---|---|---|
| Example No | Cinnamic Acid Derivative | DS (%) | UV Irradiation of Bothe side (min) | Degree of Gelation (%) | Wet Tensile Strength (g/mm²) |
| 69 | (3a-3) | 0.6 | " | 87 | 32 |
| 70 | (3a-3) | 0.3 | " | 94 | 77 |
| 71 | (1a-14) | 1.0 | " | 91 | 25 |
| 72 | (1a-1) | 0.9 | " | 99 | 85 |
| 73 | (1a-2) | 1.2 | " | 98 | 66 |
| 74 | (1a-3) | 0.4 | " | 98 | 35 |
| 75 | (1a-4) | 0.6 | " | 92 | 32 |
| 76 | (1a-5) | 1.2 | " | 97 | 42 |
| 77 | (1a-6) | 0.6 | " | 96 | 37 |
| 78 | (1a-8) | 0.7 | " | 94 | 4 |
| 79 | cinnamic anhydride | 2.0 | " | 85 | Not Detected |

As described above, this invention of a cinnamic acid derivative containing a. spacer enables the synthesis of cinnamic acid-polysaccharide derivatives, particularly cinnamic acid-glycosaminoglycans, which have high sensitivity and high efficiency of photoreaction and, hence, the provision of crosslinked cinnamic acid-glycosaminoglycan derivatives retaining the inherent beneficial properties of the glycosaminoglycan such as bioresorption, biocompatibility, no toxicity, no antigenicity, and high water absorption.

While the invention has been described in detail and with reference to specific examples thereof, it will be apparent to one skilled in the art that various changes and modifications can be made therein without departing from the spirit and scope thereof.

What is claimed is:

1. A cinnamic acid-polysaccharide derivative represented by any of the formulas (13)–(15):

 (13)

 (14)

 (15)

wherein $R^1$ represents a group of the formula (4):

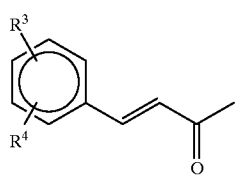 (4)

wherein $R^3$ and $R^4$ independently represent a hydrogen atom, a nitro group, an amino group hydroxyl group or a $C_{1-4}$ alkoxy group;

$R^2$ represents a group of the formula (5):

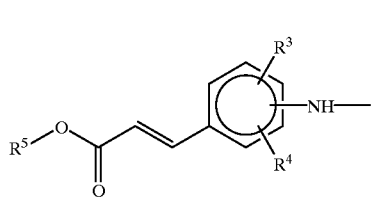 (5)

wherein $R^3$ and $R^4$ are as defined above; $R^5$ represents a lower alkyl group;

—A represents an amino- and hydroxy-containing compound residue represented by any of the formulas (6')–(9'):

 (6')

wherein n represents a whole number of 3-18,

 (7')

wherein m represents a whole number of 2-10,

 (8')

wherein $R^6$ represents a hydrogen atom or a lower alkyl group;
$R^7$ represents a lower alkyl group,

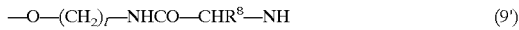 (9')

wherein l represents a whole number of 2–18; $R^8$ represents the side chain of an α-amino acid residue;

—B represents an amino acid residue of the formula (10'):

 (10')

wherein k represents a whole number of 1–18;

—C represents an amino acid residue of the formula (11') or (12');

 (11')

wherein k is as defined above,

 (12')

wherein i represents a whole number of 1–6; $R^8$ is as defined above;

$P^1$ represents a carboxy-containing polysaccharide residue; $P^2$ represents a hydroxy-containing polysaccharide residue; and the A—$P^1$ linkage is the amide bond between the terminal amino residue of the formula (6'), (7'), (8') or (9') and the carboxyl residue of $P^1$; the B—$P^2$ linkage is the ester bond formed between the terminal carboxyl residue of the formula (10') and the hydroxyl residue of $P^2$; and the C—$P^1$ linkage is the amide bond between the terminal amino residue of the formula (11') or (12') and the carboxyl residue of $P^1$;

with the provisos that the polysaccharide is a hyaluronic acid and the photodimerizable-crosslinkable group is introduced into the cinnamic acid-polysaccharide derivative at a degree of substitution of 0.05–5.0% to a repeating constituent saccharide unit of the hyaluronic acid.

2. The cinnamic acid-polysaccharide derivative of claim 1 wherein the photodimerizable-crosslinkable group is introduced into the cinnamic acid-polysaccharide derivative represented by the formula (15) at a degree of substitution of 0.05–5.0% to a repeating constituent saccharide unit of the polysaccharide, and the polysaccharide is a hyaluronic acid.

3. The cinnamic acid-polysaccharide derivative of claim 2 wherein the hyaluronic acid has a number average molecular weight of 100,000–5,000,000.

4. The cinnamic acid-polysaccharide derivative of claim 1 wherein the cinnamic acid-polysaccharide derivative is represented by the formula (13).

5. The cinnamic acid-polysaccharide derivative of claim 1 wherein —A represents an amino- and hydroxy-containing compound residue represented by the formula (6').

* * * * *

UNITED STATES PATENT AND TRADEMARK OFFICE
CERTIFICATE OF CORRECTION

PATENT NO. : 6,025,444
DATED : February 15, 2000
INVENTOR(S) : Michinori Waki, Kenji Miyamoto, Yoshihiro Motani It is certified that error appears in the above-identified patent and that said Letters Patent is hereby corrected as shown below:

Delete "Fuji Photo Film Co., Ltd." from the Assignee and include only Seikagaku Kogyo Kabushiki Kaisha (Seikagaku Corporation)

Signed and Sealed this

Twenty-third Day of October, 2001

Attest:

NICHOLAS P. GODICI
*Attesting Officer*   *Acting Director of the United States Patent and Trademark Office*